(12) United States Patent
Glucksmann et al.

(10) Patent No.: US 7,534,579 B2
(45) Date of Patent: May 19, 2009

(54) 14273 RECEPTOR, A NOVEL G-PROTEIN COUPLED RECEPTOR

(75) Inventors: Maria Alexandra Glucksmann, Lexington, MA (US); Fong-Ying Tsai, Newton, MA (US)

(73) Assignee: Millennium Pharmaceuticals, Inc., Cambridge, MA (US)

( * ) Notice: Subject to any disclaimer, the term of this patent is extended or adjusted under 35 U.S.C. 154(b) by 233 days.

(21) Appl. No.: 11/283,567

(22) Filed: Nov. 18, 2005

(65) Prior Publication Data

US 2006/0177899 A1 Aug. 10, 2006

Related U.S. Application Data

(60) Continuation of application No. 10/171,027, filed on Jun. 12, 2002, now abandoned, which is a division of application No. 09/456,455, filed on Dec. 8, 1999, now Pat. No. 6,448,005, which is a continuation-in-part of application No. 09/261,599, filed on Feb. 26, 1999, now Pat. No. 6,395,877, which is a continuation-in-part of application No. 09/223,538, filed on Dec. 30, 1998, now abandoned, which is a continuation-in-part of application No. 09/107,761, filed on Jun. 30, 1998, now abandoned.

(51) Int. Cl.
G01N 33/53 (2006.01)
G01N 33/537 (2006.01)
G01N 33/567 (2006.01)

(52) U.S. Cl. .................. 435/7.92; 435/7.1; 435/7.2; 435/7.21; 435/7.72; 436/503; 436/501

(58) Field of Classification Search .................. None
See application file for complete search history.

(56) References Cited

U.S. PATENT DOCUMENTS

| 5,576,296 A | 11/1996 | Barfai et al. |
| 5,756,460 A | 5/1998 | Evans et al. |
| 5,789,223 A | 8/1998 | Bergsma et al. |
| 6,110,693 A | 8/2000 | Barak et al. |

FOREIGN PATENT DOCUMENTS

| WO | WO 96/14331 A1 | 5/1996 |
| WO | WO 98/15570 | 4/1998 |
| WO | WO 99/38972 A2 | 1/1999 |
| WO | WO 99/33982 A2 | 7/1999 |
| WO | WO 00/00611 A2 | 1/2000 |

OTHER PUBLICATIONS

Lahana R., Drug Discovery Today, 4(10)447-448, 1999.*
Horrobin, DF, British Med. Journal, 322(7280)239, Jul. 2003.*
Milligan, J.F. et al., J. Med. Chem. 36:14(1923-1937)1993.*
Bowie et al., 1990, Science 247:1306-1310, especially p. 1306.*
Alexander et al., Proc. Natl. Acad. Sci. 89(3352-3356)1992.*
Bowles, et al, "Gene Mapping of Familial Autosomal Dominant Dilated Cardiomyopathy to Chromosome 10q21-23", *Journal of Clinical Investigation*, vol. 98, No. 6, (1996), pp. 1355-1360.
MacLellan, et al., "Death by Design: Programmed Cell Death in Cardiovascular Biology and Diease," *Circulation Research*, vol. 82, No. 2, (Aug. 1997), pp. 137-144.
Yamazaki, et al., "The Renin-Angiotensin System and Cardiac Hypertrophy," *Heart*, vol. 76, No. (3S)3, (1996), pp. 33-35.
Glennon, et al., "Cellular Mechanisms of Cardiac Hypertrophy," *British Heart Journal*, vol. 73, No. 6, (1995), pp. 496-499.
Nucleotide Sequence Database EMBL Accession No. AA413234, May 5, 1997, 93% Identity with Seq. ID:5 nt.18-186 Reverse Orientation, XP002125904.
Nucleotide Sequence Database EMBL Accession No. AA030752, Aug. 23, 1996, 87% Identity with Seq. ID:2 nt.755-1118, 99% Identity with Seq. ID:5 nt.904-1269, XP002125905.
Nucleotide Sequence Database EMBL Accession No. AA647793, Nov. 5, 1997, 81% Identity with Seq. ID:2 nt.442-857, 96% Identity with Seq. ID:5 nt.593-1008, XP002125906.
Stadel, et al., "Orphan G Protein-Coupled Receptors: A Neglected Opportunity for Pioneer Drug Discovery," *Trends in Pharmacological Sciences*, vol. 18, No. 11, (1997), pp. 430-437.
Mills, A., et al., "Orphan Seven Transmembrane Domain Receptors: Reversing Pharmacology," *Trends in Biotechnology*, vol. 12, (1994), pp. 47-49.
Lee, N.H., et al., "Molecular Biology of G-Protein-Coupled Receptors," *Drug News and Perspectives*, vol. 6, No. 7, (1993), pp. 488-497.
Oliveira, L., et al., "A Common Motif in G-Protein-Coupled Seven Transmembrane Helix Receptors," *Journal of Computer-Aided Molecular Design*, vol. 7, No. 6, (1993), pp. 649-658.
Chatelain, et al., "Cardiac Ischaemia: Possibilities for Future Drug Therapy," *European Journal of Medicinal Chemistry*, vol. 32, (1997), pp. 687-707.
Wallace, et al., *Methods Enzymology*, vol. 152, (1987), pp. 432-443.
Sambrook, et al., *Molecular Cloning A Laboratory Manual*, (1989), pp. 11-47.

(Continued)

*Primary Examiner*—Olga N Chernyshev

(57) ABSTRACT

The present invention relates to a newly identified receptor belonging to the superfamily of G-protein-coupled receptors. The invention also relates to polynucleotides encoding the receptor. The invention further relates to methods using the receptor polypeptides and polynucleotides as a target for diagnosis and treatment in receptor-mediated disorders, specifically, cardiovascular diseases, including congestive heart failure. The invention further relates to drug-screening methods using the receptor polypeptides and polynucleotides to identify agonists and antagonists for diagnosis and treatment. The invention further encompasses agonists and antagonists based on the receptor polypeptides and polynucleotides. The invention further relates to procedures for producing the receptor polypeptides and polynucleotides.

4 Claims, 15 Drawing Sheets

OTHER PUBLICATIONS

Barak, Larry S., et al, "A β-Arrestin/Green Fluorescent Protein Biosensor for Detecting G Protein-Coupled Receptor Activation", *The Journal of Biological Chemistry*, vol. 272, No. 44, (1997), pp. 27497-27500.

Silverman, Lauren, et al, "New Assay Technologies for High-Throughput Screening", *Current Opinion in Chemical Biology*, vol. 2, (1998), pp. 397-403.

Lahana R., "How Many Leads from HTS?, " *Drug Discovery Today*, vol. 4, No. 10, pp. 447-448, (Oct. 1999).

Horrobin, D.F., *British Medical Journal*, vol. 322, No. 7280, pp. 239, (Jul. 2003).

Milligan, J.F., "Current concepts in antisense drug design," *Journal of Medicinal Chemistry*, vol. 36, No. 14, pp. 1923-1937, (1993).

Bowie, et al., "Deciphering the message in protein sequences: tolerance to amino acid substitutions," *Science*, vol. 247, pp. 1306-1310, (Mar. 16, 1990).

Alexander, et al., "Altering the antigenicity of proteins," *Proceedings of the National Academy of Sciences*, vol. 89, pp. 3352-3356, (1992).

\* cited by examiner

```
Input file F1h14273new; Ouput File F1h14273tra
Sequence length 1743

M   S   P   E   C   A   R   A   A      9
TCCGGACTAGTTCTAGACCGCTGCGGGCCGCCAGGGCCGGGA ATG TCC CCT GAA TGC GCG CGG GCA GCG     27

G   D   A   P   L   R   S   L   E   Q   L   V   T   R   T   P   F   F   S     29
GGC GAC GCG CCC TTG CGC AGC CTG GAG CAA CTG GTG GAG ACC CGC ACC CCC TTC TTC TCC    87

D   V   K   G   D   H   R   L   V   N   V   A   V   T   V   A   P   V   L     49
GAC GTC AAG GGC GAC CAC CGG CTG GTG AAC GTG GCC GTG ACC GTG GCG CCC GTG CTC       147

I   F   A   V   S   L   A   C   L   V   L   F   C   A   D   R   F   I   R     69
ATC TTT GCA GTG TCG GCG ACT GCC TGC CTC GTA CTC TTC TGC GCG GAC CGA TTC ATC CGA   207

R   R   G   A   T   L   A   V   R   W   T   E   A   W   L   G   P   V   L     89
CGC CGG GGC GCG ACT GCG GTG CGG TGG ACT GAG GCC TGG CTG GGC CCC GTT CTG          267

S   A   I   P   L   L   V   L   G   A   W   L   L   G   L   L                 109
AGC GCT ATC CCT CTG GTG CTG GGC GCC TGG CTG CTG GGC CTG CTG                     327

A   H   L   L   F   Y   V   M   T   L   S   G   S   V   I   T   L   T   L     129
GCC CAC CTG CTC CTC TTC TAC GTG ATG ACC CTG AGC GGG GTC ATC ACC CTC ACG CTG     387

A   V   S   L   E   R   M   C   I   V   H   L   Q   G   Y   R   V   R   G     149
GCC GTC AGC CTG GAG CGC ATG TGC ATC GTG CAC CTG CAG CGC GTG TAT CGG GGT         447

P   G   R   R   A   A   V   L   L   A   L   I   W   G   Y   S   A   V   A     169
CCT GGC CGG CGG GCA GCA GTG CTG CTG GCG CTC ATC TGG GCC TAT TCG GCG GTC GCC     507

A   L   P   L   C   V   F   F   R   V   P   Q   R   L   P   G   A   D   Q     189
GCT CTG CCT CTC TGC GTC TTC TTT CGA GTC CCG CAA CGG CTC CCC GGC GCC GAC CAG     567
```

| | | | | | | | | | | | | | | | | | | | |
|---|---|---|---|---|---|---|---|---|---|---|---|---|---|---|---|---|---|---|---|
| E | I | S | I | C | T | L | I | W | P | T | I | P | G | E | I | S | W | D | V | 209 |
| GAA | ATT | TCG | ATT | TGC | ACA | CTG | ATT | TGG | CCC | ACC | ATT | CCT | GGA | GAG | ATC | TCG | TGG | GAT | GTC | 627 |
| S | F | V | T | L | N | F | L | V | P | G | L | I | V | I | S | Y | K | | 229 |
| TCT | TTT | GTT | ACT | TTG | AAC | TTC | TTG | GTG | CCA | GGA | CTG | ATC | GTG | ATC | AGT | TAC | AAA | | 687 |
| I | L | Q | I | T | K | A | S | R | K | D | I | V | S | L | A | Y | S | E | 249 |
| ATT | TTA | CAG | ATC | ACA | AAG | GCA | TCA | AGG | AAG | GAC | ATC | GTG | AGC | CTG | GCC | TAC | TCG | GAG | 747 |
| S | H | Q | I | R | V | S | Q | Q | D | F | R | L | V | F | T | L | F | L | 269 |
| AGC | CAC | CAG | ATC | CGC | GTG | TCC | CAG | CAG | GAC | TTC | CGG | CTC | GTA | TTC | ACC | CTC | TTC | CTC | 807 |
| M | V | S | F | I | M | W | S | P | I | I | I | T | R | I | L | I | L | I | 208 |
| ATG | GTC | TCC | TTC | ATC | ATG | TGG | AGC | CCC | ATC | ATC | ATC | ACC | CGC | CTC | CTC | ATC | CTG | ATC | 867 |
| Q | N | F | K | Q | D | L | V | I | W | P | S | L | F | F | W | V | V | A | F | 309 |
| CAG | AAC | TTC | AAG | CAA | GAC | CTG | GTC | ATC | TGG | CCG | TCC | CTC | TTC | TTC | TGG | GTG | GTG | GCC | TTC | 927 |

FROM FIG. 1A.

FROM FIG. 1B.

```
 T   F   A   N   S   A   L   N   P   I   L   Y   N   M   T   L   C   R   N   E   329
ACA TTT GCT AAT TCA GCC CTA AAC CCC ATC CTC TAC AAC ATG ACA CTG TGC AGG AAT GAG 987

W   K   K   I   F   C   C   F   W   F   P   E   K   G   A   I   L   T   D   T   349
TGG AAG AAA ATT TTT TGC TGC TTC TGG TTC CCA GAA AAG GGA GCC ATT TTA ACA GAC ACA 1047

S   V   K   R   N   D   L   S   I   I   G   *                                   362
TCT GTC AAA AGA AAT GAC TTG TCG ATT ATT GGC TAA                                  1086

TTTTCTTTATAGCCGAGTTCTCACACCTGGGCGAGCTGTGCATGCTTTAAACAGAGTTCATTTCCAGTACCCTCCA
TCAGTGCACCCTGCTTTAAGAAAATGAACCTATGCAAATAGACATCCACAGCGTCGGTAAATTAAGGGGTGATCACCAA
GTTCATAATATTTCCCTTTATAAAGGATTTGTTGGCCAGGTGCAGTGGTTCATGCCTGTAATCCCAGCAGTTTGGG
AGGCTGAGGTGGGTGGATCACCTGAGGTCAGGAGTTCGAGACCAACATGGTGAGACCCCGTCTCTACTA
AAAATAAAAAAAAAAAAATTAGCTGGGAGTGGTGGTGGGCACCTGTAATCCTAGCTACTTGGGAGGCTGAACCAGGAGAAT
CTCTTGAACCTGGAGGCAGAGGTTGCAGTGAGCCGAGATCGTGCCATTGCACTCCAACCAGGCAACAGAGTGAAAC
TCCATCTTAAAAAAAAAAAAAAAGATTTGTTATGGGTTCCTTTAAATGTGAACTTTTTAGTGTGTTTGTAATATG
ATCAAATTTAATAAATATTTATTTATGACTGTTCAGCAAAAAAAAAAAAAAAAGGGCGG
```

RTA01/2057957v1

FIG. 1C.

```
Sequence  Description                                           score  E-value  N
7tm_1     PF00001 7 transmembrane receptor (rhodopsin           119.9  4.7e-37  1
Parsed for domains:
Sequence  Domain  seq-f  seq-t  hmm-f  hmm-t    score  E-value
7tm_1     1/1     57     321    1      259  [ ]  119.9  4.7e-37
Alignments of top-scoring domains:
7tm_1: domain 1 of 1, from 57 to 321: score 119.9, E = 4.7e-37
                *->GNlLVilvilrtkklrtptnifiINLAVADLLflltlppwalyylvg
                   GN+ ++++++r +++r +t +++INL ADLLf  + p++ ++  -+
    F1h14273,  57  GNVCALVLVAR-RRRRGATACLVLNLFCADLLFISAIPLVLAVR-WT  101 gaadWpfGsalCklvtaldvvnmyaSillLtalSiDRYlAlvhPlryrrr
                 e W++G++ C+l+ +++++++ + il+L+a S++R + Iv 1+  +r
    F1h14373, 102  --EAWLLGPVACHLLFYYMTLSGSVTILTLAAVSLERMVCIV-HLQRGVR  148 rtsprrAkvviiIvwvlalllslPpllfswvktveegngtlnvnvevCli
                +r  +v+++1+W  ++++IP  +f+ v+     ++   ++ ++ +C++
    F1h14273, 149  GPGRRARAVLLALIWGYSAVAALPLCVFFRVVPQRLPG--ADQEISICTL  196 dfpccstasvstwlrsyvllstlwgFllPllvilvcYtrllrtlr.....
                +p++++       ++s+ +++ ++ Fl+P lvl++ Y+ Il + + ++++
    F1h14273, 197  IWPTIPG------EISWDVSFVTLNFLVPGLVIVISYSKILQITKasrkr  240

..................kaaktllvvvvvFvlCWlPyflvllldtlc
                + +   +++++ + ++++ ++ ++tl+++++v F++ W P  l++ll  +
    F1h14273, 241  lcvslayseehqirvsqqdfRLFRTLFLLMVSFFIMWSPIIITILLILIQ  290

.lsilmsstCelervlptallvtlwLayvNsclNPilY<-*
                -+        +  + p ++++ +  ++++Na+lNPi+Y
    F1h14273, 291  nFK-------QDLVIWPSLFFWVVAPTFANSALNPILY           321
```

FIG. 2.

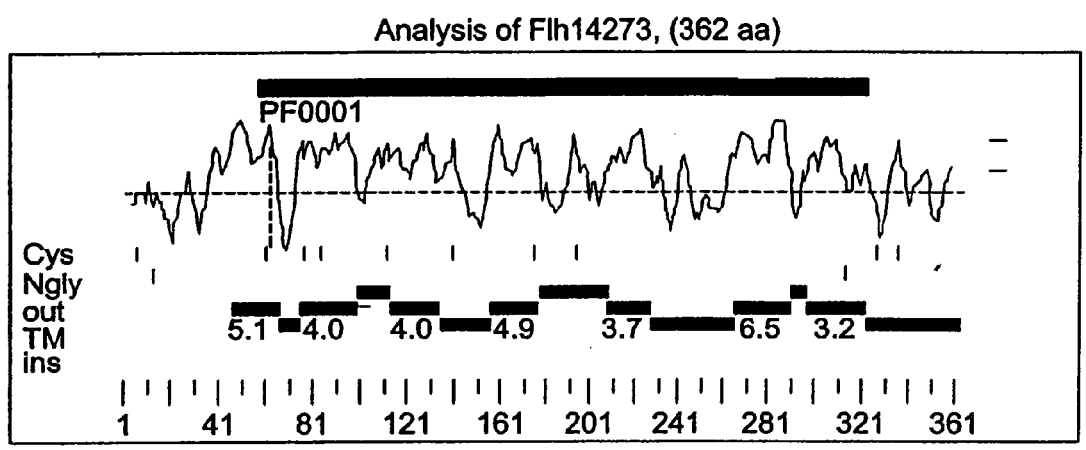

Analysis of Flh14273, (362 aa)

>Flh14273, 1086 bases, 1825 checksum.
MSPECARAAQDAPLRSLEQANRTRFPFFSDVKGDHRLVLAAVETTVLVLEFAVSLLGNVC
ALVLVARRRRRGATAQLVLNLFCADLLFYSAIPLVLAVRWTEAVLLGPVACHLLFYVMTL
SGSVTILTLAAVSLERMVCIVHLQRCVRGPGRRARAVLLALIWGYSAVAALPLCVFFRVV
PQRLPGADQEISICTLIWPTIPGEISWDVSFVTLNFLVPGLVIVISYSKILQITKASRKR
LTVSLAYSESHQIRVSQQDFRLFRTLFLLMVSFFIMWSPIIITILLILIQNFKQDLVIWP
SLFFWVVAFTFANSALNPILYNMTLCRNEWKKIFCCFWFGPEKGAILTDTSVKRNDLSIIS
G+

FIG. 4.

Prosite Pattern Matches for F1h14273

>PS00001/PD0C00001/ASN_GLYCOSYLATION N-glycosylation site.

Query: 21    NRTR    24
Query: 322   NMTL    325

>PS00004/PD0C00004/CAMP_PHOSPHO_SITE cAMP- and cGMP-dependent protein kinase phosphorylation site.

Query: 239   KRLT    242

>PS00005/PD0C00005/PKC_PHOSPHO_SITE Protein kinase C phosphorylation site.

Query: 237   SRK    239
Query: 350   SVK    352

>PS00006/PD0C00006/CK2_PHOSPHO_SITE Casien kinase II phosphorylation site.

Query: 256   SQQD    259

>PS00008/PD0C00008/MYRISTYL N-myristoylation site.

Query: 57    GNVCAL    62
Query: 72    GATACL    77
Query: 343   GAILTD    348

>PS00009/PD0C00009/AMIDATION Amidation site.

Query: 150   PCRR    153

>PS00029/PD0C00029/LEUCINE_ZIPPER Leucine zipper pattern.

Query: 106   LGPVACHLLFYVMTLSGSVTIL    127

FIG. 5.

Transmembrane Segments Predicted by MEMSAT

| Start | End | Orient | Score |
|---|---|---|---|
| 46 | 66 | out->ins | 5.1 |
| 75 | 98 | ins->out | 4.0 |
| 113 | 134 | out->ins | 4.0 |
| 156 | 177 | ins->out | 4.9 |
| 209 | 227 | out->ins | 3.7 |
| 266 | 289 | ins->out | 6.5 |
| 297 | 321 | out->ins | 3.2 |

\>F1h14273,
MSPECARAAGDAPLRSLEQANRTRFPFFSDVKGDHRLVLAAVETTVLVLIPAVSLLGNVC
ALVLVARRRRRGATACLVLNLFCADLLFISAWPLVLAVRWTEAWLLGPVACHLLFYVMTL
SGSVTILTLAAVSLERMVCIVHLQRGVRGPGRRARAVLLALIWGYSAVAALPLCVFFRVV
PQRLPGADQEISICTLIWPTIPGEISWDVSFVTLNFLVPGLVIVISYSKILQITKASRKR
LTVSLAYSESHQIRVSQQDFRLFRTLFLLMVSFFIMWSPIIITILLILIQNFKQDLVIWP
SLFFWVVAFTFANSALNPILYNMTLCRNEWKKIFCCFWFPEKGAILTDTSVKRNDLSIIS
G

Transmembrane Segments for Presumed Mature Peptide

| Start | End | Orient | Score |
|---|---|---|---|
| 14 | 37 | ins->out | 4.0 |
| 52 | 73 | out->ins | 4.0 |
| 95 | 116 | ins->out | 4.9 |
| 148 | 166 | out->ins | 3.7 |
| 205 | 228 | ins->out | 6.5 |
| 236 | 260 | out->ins | 3.2 |

\>F1h14273,_mature
LVLVARRRRRGATACLVLNLFCADLLFISAIPLVLAVRWTEAWLLGPVACHLLPYVMTLS
GSVTILTLAAVSLERMVCIVHLQRGVRGPGRRARAVLLALIWGYSAVAALPLCVFFRVVP
QRLPGADQEISICTLIWPTIPGEISWDVSFVTLNFLVPGLVIVISYSKILQITKASRKRL
TVSLAYSESHQIRVSQQDFRLFRTLFLLMVSFFIMWSPIIITILLILIQNFKQDLVIWPS
LFFWVVAFTFANSALNPILYNMTLCRNEWKKIPCCFWFPEKGAILTDTSVKRNDLSIISG

```
Input file 14273m; Output File 14273mtra
Sequence length 1560

TTGCCAAGCTCAGCGTAAGCCTCTTCCACTGCAATCTTCACAGAAGGGGTTCATGGAGTGCTTCACACCATCAGTGACCA

CTCCAGACTTGTCCGGCTTTACCCGAATCTTCACAGCGGAGTCGATGACCCTCTTGACAGCCACGAGCGCGGCGAGCTC

M   S   P   E   C   A   Q   T   T   G      10
CGGCCATCTTCCCGGACGCGGTGGGCCCGGC ATG TCC CCT GAG TGT GCA CAG ACG ACG GGC              30
 P   G   P   S   H   T   L   D   Q   V   N   R   T   H   F   P   F   F   S   D      30
CCT GCT CCC TCG CAC ACC CTG GAC CAA GTC AAT CGC ACC CAC TTC CCT TTC TTC TCG GAT      90
 V   K   G   D   H   R   L   V   L   G   S   V   E   T   T   V   L   G   L   I      50
GTC AAG GGC GAC CAC CGG TTG GTG TTG AGC GTC GAG ACC ACC GTT CTA GGA CTC ATC         150
 F   V   V   S   L   L   G   N   V   L   C   L   V   L   V   A   R   R   R          70
TTT GTC GTC TCA CTG CTG GGC AAC GTG CTC CTA GCT GCT GTG CGC CGT CGG CGC             210
 R   G   A   S   L   V   L   V   N   L   F   C   A   D   L   L   F   T   S          90
CGT GGG GCG TCA GCC AGC CTG GTG CTC GTG AAC CTC TTC TGC GCG GAT TTG CTC TTC ACC AGC  270
 A   I   P   L   L   V   R   W   T   E   A   G   S   S   V   T   G   P   V          110
GCC ATC CCT CTA GTG CGC TGG ACT GAG GCC AGC AGC GTC ACG GGG CCC GTC                 330
 C   H   L   L   F   Y   L   M   V   M   S   G   S   V   T   I   L   T   L   A      130
TGC CAC CTG CTC TTC TAC GTG ATG ACA ATG AGC GGC AGC GTC ACG ATC CTC ACA CTG GCC     390
 A   V   S   L   E   R   M   V   C   I   V   R   L   R   R   G   L   S   P          150
GCG GTC AGC CTG GAG CGC ATG GTG TGC ATC GTG CGC CTC CGG CGC GGG TTG AGC CCG         450
 G   R   T   Q   A   A   L   L   W   G   Y   S   A   L   A   A   A                  170
GGG CGG CGG ACT CAG GCG GCA CTG CTG TGG GGT TAC TCG GCG CTC GCC GCG                 510
```

TO FIG. 7B.

FROM FIG. 7A.

```
L   P   L   Y   I   L   F   R   V   P   Q   R   L   P   G   G   D   Q   E        190
CTG CCC CTC TAC ATC TTG TTC CGC GTC CCG CAG CGC CTT CCC GGG GAC CAG GAA           627
I   P   I   C   T   T   L   D   W   N   P   I   G   E   I   S   W   V   F        210
ATT CCG ATT TGC ACA TTG GAT TGG AAC CCC ATA GGA GAA ATC TCA TGG GAT GTG TTT       630
F   E   T   L   N   F   L   V   P   G   R   K   I   V   T   S   Y   K   I        230
TTT GAG ACT TTG AAC TTC CTG GTG CCG GGA AGG AAG ATC GTG TCC AGT TAC AAA ATT       690
L   Q   I   K   T   A   S   R   K   R   D   L   T   S   L   A   Y   S   S        250
TTA CAG ATC ACG AAA GCA TCG CGG AAG AGG GAC CTT ACG AGC TTG GCA TAC TCT AGC       750
H   Q   R   V   S   Q   Q   Y   I   I   R   F   T   L   F   L   L   M   Q        270
CAC CAG ATC CGA GTG TCC CAA CAA TAC ATA CGA TTC ACG CTC TTC CTC CTG ATC CAA       810
V   S   F   I   M   W   V   D   P   I   S   F   F   W   L   L   V   I   Q        290
GTT TCC TTC ATC ATG TGG GTC GAC CCC ATC TCC TTT TTC TGG CTG GTG ATC CAA           870
N   F   R   Q   S   A   D   L   N   P   L   Y   F   F   M   S   L   R   T        310
AAC TTC CGG CAG CAG TCT GCC GAC CTA AAC CCC ATA CTG TTT TTC ATG TCG CTG ACG       930
F   A   N   S   A   I   F   C   F   F   P   E   K   G   A   I   F   N   E   W    330
TTT GCC AAC TCT GCC ATT TTT TGC TGC TTT TTT CCA GAG AAG GGA GCC ATT TTC AAC GAA   TGG
                                                                                   990
R   K   I   R   R   N   D   L   S   V   L   F   P   T   D   T   S               350
AGG AAG ATT CGA AGG CGA AAT GAC TTG TCT GTT TCT ATT TCC AGC TAA                  1050
V                                                                                 362
GTC                                                                              1086
```

CTAGCCTCTGGTGCCAGGTGAACCACGGTGTGCATGTAAAGGAGTTAACTTCAAGGAAAGCCCACCAGTGCGCCCTGC
TTTAAAATACCCGACTTCCAACAGCAGGCATCTACGGAGCAGCAAATTAAGGAATGATCGCTCAGTATAAAAATATT
TTTCCTTAAAGAGAACTTTCTATGGGTTCCTTTGTGAACTTTTTAAGTGTGTTTGTAATATGATCTAGTAATAAATT
TTTATTTATAACGTGTTCCTACAAAAAAAAAAAAAAAAAAAAAA

FIG. 7B.

```
Query:    14273m,
Scores for sequence family classification (score includes all domains):
Sequence  Description                                      Score   E-value  N
7tm_1     PF00001    7 transmembrane receptor (rhodopsin   118.8   1e-35    1
Parsed for domains:
Sequence  Domain  seq-f  seq-t  hmm-f  hmm-t     score   E-value   -
7tm_1     1/1      57    321 ..    1    259 [ ]  118.8   1e-36
Alignments of top-scoring domains:
7tm_1: domain 1 of 1, from 57 to 321: score 118.8, E = 1e-36
              *->GNlLVilvilrtkklrtptniflINLAvADLLflltlppwalyylvg
                 GN+ ++++++r +++r ++ +++lNL  ADLLf+ + p++ ++  ++
   14273m,  57   GNVCALVLVAR-RRRRGASASLVLNLFCADLLFTSAIPLVLVVR-WT 101 gaadWpfGaalCklvtaldvvnmyaSill1LtalSiDRY1AlvhPlryrrr
              e W++G+++C+l+ +++++++ + il+L+a S++R + Iv  lr   +
   14273m, 102 --EAWLLGPVVCHLLPYVMTMSGSVTILTLAAVSLERMVCIV-RLRRGLS 148 rtsprrA.kvvillvWvlallls1Ppllfswvktveagngtlnvnvtv Cl
              rr++++++++++W ++l++lP ++++ v +   ++g    ++ +C+
   14273m, 149 GP-GRRTqAALLAFIWGYSALAALPLYILFRVVPQRLPGGD--QEITPCT 195 idfpeestasvstwlrsyvllstlvgF2lPllvilvoYtrllrtlr....
              +d+p++ +      ++s+ +++ ++ Fl+P lvl++ Y+ ll + + +++
   14273m, 196 LDWPNRIG------EISWDVFFETLNFLVPGLVIVISYSKILQITKasrk 239

...................kaaktllvvvvvFvlCWlPyfivllldt-
              + + +    +++++ + ++++ ++ +tl+++++v F++ W P  i++ll  +
   14273m, 240 rltlslayseshqIrvsqqdyRLFRTLFLLMVSFFIMWSPIIITILLILI 289 c.lalimestCelervlptallvtlwLayvNsclNPilY<-*
              ++      +  + p ++++ + ++++Ns+lNPl+Y
   14273m, 290 QnFR-------QDLVIWPSLFFWVVAFTFANSALNPILY 321
```

FIG. 8.

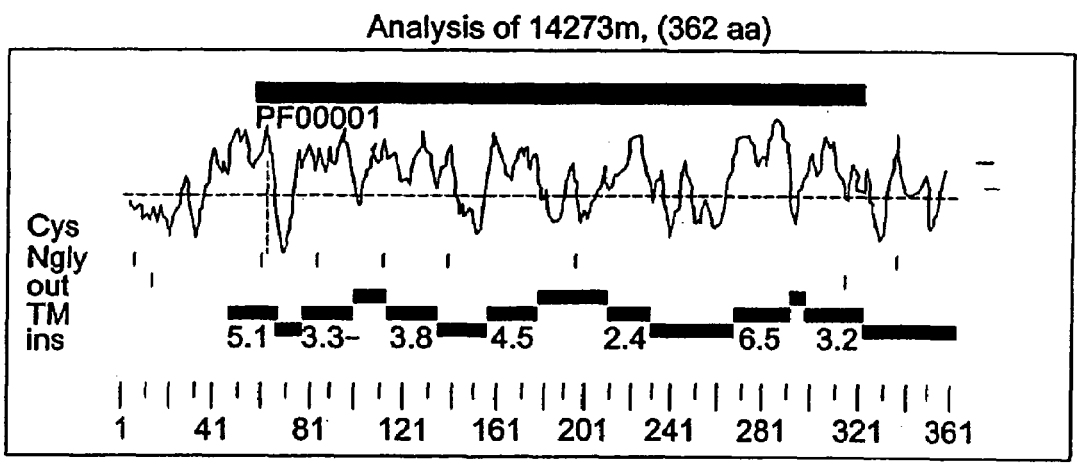

Analysis of 14273m, (362 aa)

>14273m, 1086 bases, 6943 checksum.
MSPECAQTTGPCPSHTLDQVNRTHFPFFSDVKGDHRLVLSVVETTVLGLIFVVSLLGNVC
ALVLVARRRRRGASASLVLNLFCADLLFTSAIPLVLVVRWTEAWLLGPVVCHLLFVVMTM
SGSVTILTLAAVSLERMVCIVRLRRGLSGPGRRTQAALLAFIWGYSALAALPLYILFRVV
PQRLPGGDQEIPICTLDWPNRIGEISWDVFFETLNFLVPGLVIVISYSKILQITKASRKR
LTLSLAYSESHQIRVSQQDYRLFRTLFLLMVSFFIMWSPIIITILLILIQNFRQDLVIWP
SLFFWVVAFTFANSALNPILYNMSLFRNEWRKIFCCFPFPEKGAIFTDTSVRRNDLSVIS
S*

FIG. 10.

Prosite Pattern Matches for 14273m,

>PS00001/PDOC00001;ASN_GLYCOSYLATION N-glycosylation site.

Query: 21      NRTH    24
Query: 322     NRTH    325

>PS00002/PDOC00002/GLYCOSAMINOGLYCAN Glycosaminoglycan attachment site.
    RU    Additional rules:
    RU    There must be at least two acidic amino acids (Glu or Asp) from -2 to
            -4 relative to the serine.
Query: 148     SGPG    151

>PS00004/PDOC00004/CAMP_PHOSPHO_SITE cAMP- and cGMP-dependent protein kinase phosphorylation Query: 239     KRLT    242

>PS00005/PDOC00005/PKC_PHOSPHO_SITE Protein kinase C phosphorylation site.

Query: 237     SRK     239
Query: 350     SVR     352

>PS00006/PDOC00006/CK2_PHOSPHO_SITE Casein kinase II phosphorylation site.

Query: 40      SVVE    43
Query: 256     SQQD    259

>PS00008/PDOC00008/MYRISTYL N-myristoylation site.

Query: 57      GNVCAL  62
Query: 72      GASASL  77
Query: 343     GAIFTD  348

>PS00009/PDOC00009/AMIDATION Amidation site.

Query: 150     PGRR    153

FIG. 11.

Transmembrane Segments Predicted by MEMSAT

| Start | End | Orient | Score |
|---|---|---|---|
| 46 | 66 | out->ins | 5.1 |
| 77 | 98 | ins->out | 3.3 |
| 113 | 134 | out->ins | 3.8 |
| 156 | 177 | ins->out | 4.5 |
| 209 | 227 | out->ins | 2.4 |
| 266 | 289 | ins->out | 6.5 |
| 297 | 321 | out->ins | 3.2 |

>14273m,
MSPECAQTTGPGPSHTLDQVNRTHFPFFSDVKGDHRLVLSVVETTVLGLIFVVSLLGNVC
ALVLVARRRRRGASASLVLNLFCADLLFTSAIPLVLVVRWTEAWLLGPVVCHLLFYVMTM
SGSVTILTLAAVSLERMVCIVRLRRGLSGPGRRTQAALLAFIWGYSALAALPLYILFRVV
PQRLPGGDQEIPICTLDWPNRIGEISWDVFFETLNFLVPGLVIVISYSKILQITKASRKR
LTLSLAYSESHQIRVSQQDYRLFRTLFLLMVSFFIMWSPIIITILLILIQNFRQDLVIWP
SLFFWVVAFTFANSALNPILYMMSLFRNEWRKIFCCFFFPEKGAIFTDTSVRRNDLSVIS
S

Transmembrane Segments for Presumed Mature Peptide

| Start | End | Orient | Score |
|---|---|---|---|
| 16 | 37 | ins->out | 3.3 |
| 52 | 73 | out->ins | 3.8 |
| 95 | 116 | ins->out | 4.5 |
| 148 | 166 | out->ins | 2.4 |
| 205 | 228 | ins->out | 6.5 |
| 236 | 260 | out->ins | 3.2 |

>14273m,_mature
LVLVARRRRRGASASLVLNLFCADLLFTSAIPLVLVVRWTEAWLLGPVVCHLLFYVMGMS
GSVTILTLAAVSLERMVCIVRLRRGLSGPGRRTQAAIIAFIWGYSALAALPLYILFRVVP
QRLPGGDQEIPICTLDWPNRIGEISWCVFFETLNFLVPGLVIVISYSKILQITKASRKRL
TLSLAYSESKQIRVSQQDYRLFRTLFLLMVSFFTMWSPIIITILLILIQNFRQDLVIWPS
LFFWVVAFTFANSALNPILYNMSLFRNEWRKIFCCFFFPEKGAIFTDTSVRRNDLSVISS

FIG. 12.

14273 RECEPTOR, A NOVEL G-PROTEIN COUPLED RECEPTOR

RELATED APPLICATIONS

This application is a continuation of U.S. patent application Ser. No. 10/171,027, filed Jun. 12, 2002, now abandoned, which is a divisional application of U.S. patent application Ser. No. 09/456,455, filed Dec. 8, 1999, now U.S. Pat. No. 6,448,005, which is a continuation-in-part application of U.S. patent application Ser. No. 09/261,599, filed Feb. 26, 1999, now U.S. Pat. No. 6,395,877, which is a continuation-in-part of U.S. patent application Ser. No. 09/223,538, filed Dec. 30, 1998, now abandoned, which is a continuation-in-part of U.S. patent application Ser. No. 09/107,761, filed Jun. 30, 1998, now abandoned, which are hereby incorporated herein in their entirety by reference.

FIELD OF THE INVENTION

The present invention relates to a newly identified receptor belonging to the superfamily of G-protein-coupled receptors. The invention also relates to polynucleotides encoding the receptor. The invention further relates to methods using the receptor polypeptides and polynucleotides as a target for diagnosis and treatment in receptor-mediated disorders, specifically, cardiovascular diseases, including congestive heart failure. The invention further relates to drug-screening methods using the receptor polypeptides and polynucleotides to identify agonists and antagonists for diagnosis and treatment. The invention further encompasses agonists and antagonists based on the receptor polypeptides and polynucleotides. The invention further relates to procedures for producing the receptor polypeptides and polynucleotides.

BACKGROUND OF THE INVENTION

G-Protein Coupled Receptors

G-protein coupled receptors (GPCRs) constitute a major class of proteins responsible for transducing a signal within a cell. GPCRs have three structural domains: an amino terminal extracellular domain, a transmembrane domain containing seven transmembrane segments, three extracellular loops, and three intracellular loops, and a carboxy terminal intracellular domain. Upon binding of a ligand to an extracellular portion of a GPCR, a signal is transduced within the cell that results in a change in a biological or physiological property of the cell. GPCRs, along with G-proteins and effectors (intracellular enzymes and channels modulated by G-proteins), are the components of a modular signaling system that connects the state of intracellular second messengers to extracellular inputs.

GPCR genes and gene-products are potential causative agents of disease (Spiegel et al., *J. Clin. Invest.* 92:1119-1125 (1993); McKusick et al., *J. Med. Genet.* 30:1-26 (1993)). Specific defects in the rhodopsin gene and the V2 vasopressin receptor gene have been shown to cause various forms of retinitis pigmentosum (Nathans et al., *Annu. Rev. Genet.* 26:403-424(1992)), and nephrogenic diabetes insipidus (Holtzman et al., *Hum. Mol. Genet.* 2:1201-1204 (1993)). These receptors are of critical importance to both the central nervous system and peripheral physiological processes. Evolutionary analyses suggest that the ancestor of these proteins originally developed in concert with complex body plans and nervous systems.

The GPCR protein superfamily can be divided into five families: Family I, receptors typified by rhodopsin and the β2-adrenergic receptor and currently represented by over 200 unique members (Dohlman et al., *Annu. Rev. Biochem.* 60:653-688 (1991)); Family II, the parathyroid hormone/calcitonin/secretin receptor family (Juppner et al., *Science* 254: 1024-1026 (1991); Lin et al., *Science* 254:1022-1024 (1991)); Family III, the metabotropic glutamate receptor family (Nakanishi, *Science* 258 597:603 (1992)); Family IV, the cAMP receptor family, important in the chemotaxis and development of *D. discoideum* (Klein et al., *Science* 241: 1467-1472 (1988)); and Family V, the fungal mating pheromone receptors such as STE2 (Kurjan, *Annu. Rev. Biochem.* 61:1097-1129 (1992)).

There are also a small number of other proteins which present seven putative hydrophobic segments and appear to be unrelated to GPCRs; they have not been shown to couple to G-proteins. *Drosophila* expresses a photoreceptor-specific protein, bride of sevenless (boss), a seven-transmembrane-segment protein which has been extensively studied and does not show evidence of being a GPCR (Hart et al., *Proc. Natl. Acad. Sci. USA* 90:5047-5051 (1993)). The gene frizzled (fz) in *Drosophila* is also thought to be a protein with seven transmembrane segments. Like boss, fz has not been shown to couple to G-proteins (Vinson et al., *Nature* 338:263-264 (1989)).

G proteins represent a family of heterotrimeric proteins composed of α, β and γ subunits, that bind guanine nucleotides. These proteins are usually linked to cell surface receptors, e.g., receptors containing seven transmembrane segments. Following ligand binding to the GPCR, a conformational change is transmitted to the G protein, which causes the α-subunit to exchange a bound GDP molecule for a GTP molecule and to dissociate from the βγ-subunits. The GTP-bound form of the α-subunit typically functions as an effector-modulating moiety, leading to the production of second messengers, such as cAMP (e.g., by activation of adenyl cyclase), diacylglycerol or inositol phosphates. Greater than 20 different types of α-subunits are known in humans. These subunits associate with a smaller pool of β and γ subunits. Examples of mammalian G proteins include Gi, Go, Gq, Gs and Gt. G proteins are described extensively in Lodish et al., *Molecular Cell Biology*, (Scientific American Books Inc., New York, N.Y., 1995), the contents of which are incorporated herein by reference. GPCRs, G proteins and G protein-linked effector and second messenger systems have been reviewed in *The G-Protein Linked Receptor Fact Book*, Watson et al., eds., Academic Press (1994).

GPCRs are a major target for drug action and development. Accordingly, it is valuable to the field of pharmaceutical development to identify and characterize previously unknown GPCRs. The present invention advances the state of the art by providing a previously unidentified human GPCR.

SUMMARY OF THE INVENTION

It is an object of the invention to identify novel GPCRs.

It is a further object of the invention to provide novel GPCR polypeptides that are useful as reagents or targets in receptor assays applicable to treatment and diagnosis of GPCR-mediated disorders.

It is a further object of the invention to provide polynucleotides corresponding to the novel GPCR receptor polypeptides that are useful as targets and reagents in receptor assays applicable to treatment and diagnosis of GPCR-mediated disorders and useful for producing novel receptor polypeptides by recombinant methods.

A specific object of the invention is to identify compounds that act as agonists and antagonists and modulate the expression of the novel receptor.

A further specific object of the invention is to provide compounds that modulate expression of the receptor for treatment and diagnosis of GPCR-related disorders.

The invention is thus based on the identification of a novel GPCR, designated the 14273 receptor.

The invention provides isolated 14273 receptor polypeptides including a polypeptide having the amino acid sequence shown in SEQ ID NO:1 (human) and SEQ ID NO:4 (murine), or the amino acid sequence encoded by the cDNA deposited as ATCC No. PTA-1143 ("the deposited cDNA").

The invention also provides isolated 14273 receptor nucleic acid molecules having the sequence shown in SEQ ID NO:2 (human) and SEQ ID NO:5 (murine) or in the deposited cDNA.

The invention also provides variant polypeptides having an amino acid sequence that is substantially homologous to the amino acid sequence shown in SEQ ID NO: 1 or SEQ ID NO:4 or encoded by the deposited cDNA.

The invention also provides variant nucleic acid sequences that are substantially homologous to the nucleotide sequence shown in SEQ ID NO:2 or SEQ ID NO:5 or in the deposited cDNA.

The invention also provides fragments of the polypeptide shown in SEQ ID NO:1 or SEQ ID NO:4 and nucleotide shown in SEQ ID NO:2 or SEQ ID NO:5, as well as substantantially homologous fragments of the polypeptide or nucleic acid.

The inventors have linked expression of the receptor polynucleotides to cardiovascular disease and specifically to congestive heart failure. The inventors have found that receptor mRNA is induced in hypertrophic human cardiac myocytes and that expression correlates with morphological change. This induction is observed in ischemic and dilated hearts.

Therefore, the invention also provides receptor variants that correlate with the cardiovascular disorders.

Cardiac hypertrophy is the principal response of the heart to overload from any cause including ischemia/reperfusion injury, myocardial infarction, longstanding heart failure, vascular wall remodeling, ventricular remodeling, dilated cardiomyopathy, rapid ventricular pacing, coronary microembolism, pressure-overload, aortic banding, coronary artery ligation, end stage heart failure, tachyarrhythmia, bradyarrhythmia, valvar heart disease, and hypertension. Hypertrophy is a strong, independent predictor of cardiovascular death and is associated with diastolic dysfunction. Since adult cardiac myocytes are terminally differentiated cells, the increase in muscle mass seen in cardiac hypertrophy occurs predominantly by an increase in myocyte size. At the cellular level, the events leading to cardiac hypertrophy have been divided into (1) extracellular hypertrophic stimulus; (2) intracellular signal transduction; and (3) activation of nuclear events that allow for the hypertrophic phenotype.

Further experiments by the inventors have shown that in transgenic mouse models in which the novel receptor is overexpressed, the induction of cardiac hypertrophy is observed. Histological examination of hearts derived from these transgenic mice shows a significant increase in the heart:body weight ratio. In several independent sets of transgenic animals, enlargement of the heart and heart failure is a significant outcome. Observations include enlarged cardiomyocytes, biventricular dilatation, atrial thrombi, and interstitial fibrosis.

Additional experiments have shown that the 14273 receptor was upregulated in a rat pressure overload model. A rat pressure overload model was generated by placing a constrictive band around the aorta to induce a state of cardiac hypertrophy (Kimura et al. *Am. J. Physiol.* 256:H1006-H1011 (1989)). The 14273 receptor was shown to be induced at the mRNA level following banding of the aorta. This increase in expression was correlated with the hypertrophic phenotype. Results were obtained by in situ hybridization.

Additional experiments showed that in transgenic mice overexpressing the 14273 receptor, that receptor mRNA and protein levels were correlated with the severity of the phenotype. The phenotype seen in the 14273 transgenic animals ranged from severe, with death by 3-4 weeks, to mild, showing only subtle pathohistological findings, as evidenced by staining cardiac myocytes from wild-type and transgenic animals with wheat germ agglutinin or Masson's Trichrome. The wheat germ agglutinin outlines myocytes, which in turn allows the determination of the degree of hypertrophy, while the Trichrome identifies collagen fibers in tissue sections. Collagen fibers are a hallmark of fibrosis. The severity of the phenotype was correlated with increased transgene expression at both the mRNA and protein levels. Severity of the phenotype was proportional to the level of 14273 receptor expression observed. In these experiments hypertrophy was observed in both the nucleus and cytoplasm of the hypertrophic myocytes. In addition, histological results from these animals showed myocyte disorganization, as well as atrial and ventricular loss. This was then associated with subsequent interstitial fibrosis as a result of the replacement of dead myocytes with connective tissue. Fibroelastosis (deficiency in elastic fiber) was also observed. This is evidence of a loss of general elastic tone from cardiac tissue. Finally, atrial thrombosis was observed to result from the above pathological series of events. In addition, along with increased expression of the 14273 receptor, the inventors observed coordinate increased expression of atrial natriuretic factor (ANF). This factor, a natural diuretic, is produced in increased amounts during cardiac hypertrophy and, accordingly, serves as a marker of cardiac hypertrophy.

The invention also provides vectors and host cells for expressing the receptor nucleic acid molecules and polypeptides and particularly recombinant vectors and host cells. The invention particularly provides host cells that provide a model for cardiovascular diseases by containing specific variants that are correlated with the disorders.

The invention also provides methods of making the vectors and host cells and methods for using them to produce the receptor nucleic acid molecules and polypeptides.

The invention also provides antibodies that selectively bind the receptor polypeptides and fragments.

The invention also provides methods of screening for compounds that modulate the activity of the receptor polypeptides. Modulation can be at the level of the polypeptide receptor or at the level of controlling the expression of nucleic acid (RNA or DNA) expressing the receptor polypeptide.

The invention also provides a process for modulating receptor polypeptide activity, especially using the screened compounds, including to treat conditions related to expression of the receptor polypeptides.

Since the receptor polynucleotides have been linked to cardiovascular diseases, the invention provides methods for modulating receptor polypeptide and nucleic acid expression in subjects having, or predisposed to having, cardiovascular diseases, cells from these subjects, and model systems for the disorders.

The invention also provides diagnostic assays for determining the presence of and level of the receptor polypeptides or nucleic acid molecules in a biological sample.

The invention also provides diagnostic assays for determining the presence of a mutation in the receptor polypeptides or nucleic acid molecules.

Since the receptor polynucleotides have been linked to cardiovascular diseases, the invention provides diagnostic assays for determining the presence, level, or mutation of receptor polynucleotides and polypeptides preferably in subjects with, or having a predisposition to, cardiovascular diseases, cells from these subjects, and model systems for the disorders.

DESCRIPTION OF THE DRAWINGS

FIGS. 1A-1C show the human 14273 nucleotide sequence (SEQ ID NO:2) and the deduced 14273 amino acid sequence (SEQ ID NO:1). It is predicted that amino acids 1-45 of SEQ ID NO:1 constitute the amino terminal extracellular domain, amino acids 46-321 constitute the region spanning the transmembrane domain, and amino acids 322-361 of SEQ ID NO:1 constitute the carboxy terminal intracellular domain. The transmembrane domain contains seven transmembrane segments, three extracellular loops and three intracellular loops. The transmembrane segments are found from about amino acid 46 to about amino acid 66, from about amino acid 75 to about amino acid 98, from about amino acid 113 to about amino acid 134, from about amino acid 156 to about amino acid 177, from about amino acid 209 to about amino acid 227, from about amino acid 266 to about amino acid 289, and from about amino acid 297 to about amino acid 321 of SEQ ID NO:1. Within the region spanning the entire transmembrane domain are three intracellular and three extracellular loops. The three intracellular loops are found from about amino acid 67 to about amino acid 74, from about amino acid 135 to about amino acid 155, and from about amino acid 228 to about amino acid 265 of SEQ ID NO:1. The three extracellular loops are found at from about amino acid 99 to about amino acid 112, from about amino acid 178 to about amino acid 208, and from about amino acid 290 to about amino acid 296 of SEQ ID NO:1.

The transmembrane domain includes a sequence, ERM, corresponding to the GPCR signal transduction signature, DRY, at residues 135-137 of SEQ ID NO:1. The sequence includes an arginine at residue 136 of SEQ ID NO:1, an invariant amino acid in GPCRs.

FIG. 2 shows a comparison of the human 14273 receptor against the Prosite data base of protein patterns, specifically showing a high score against the seven transmembrane segment rhodopsin superfamily (SEQ ID NO:3). The underlined area shows a sequence corresponding to the GPCR signature, and specifically the position of an arginine residue, conserved in GPCRs. The most commonly conserved sequence is an aspartate, arginine, tyrosine (DRY) triplet. DRY is implicated in signal transduction. Arginine is invariant. Aspartate is conservatively placed in several GPCRs. In the present case, the arginine is found in the sequence ERM, which matches the position of DRY or invariant arginine in GPCRs of the rhodopsin superfamily of receptors.

Figure 3:
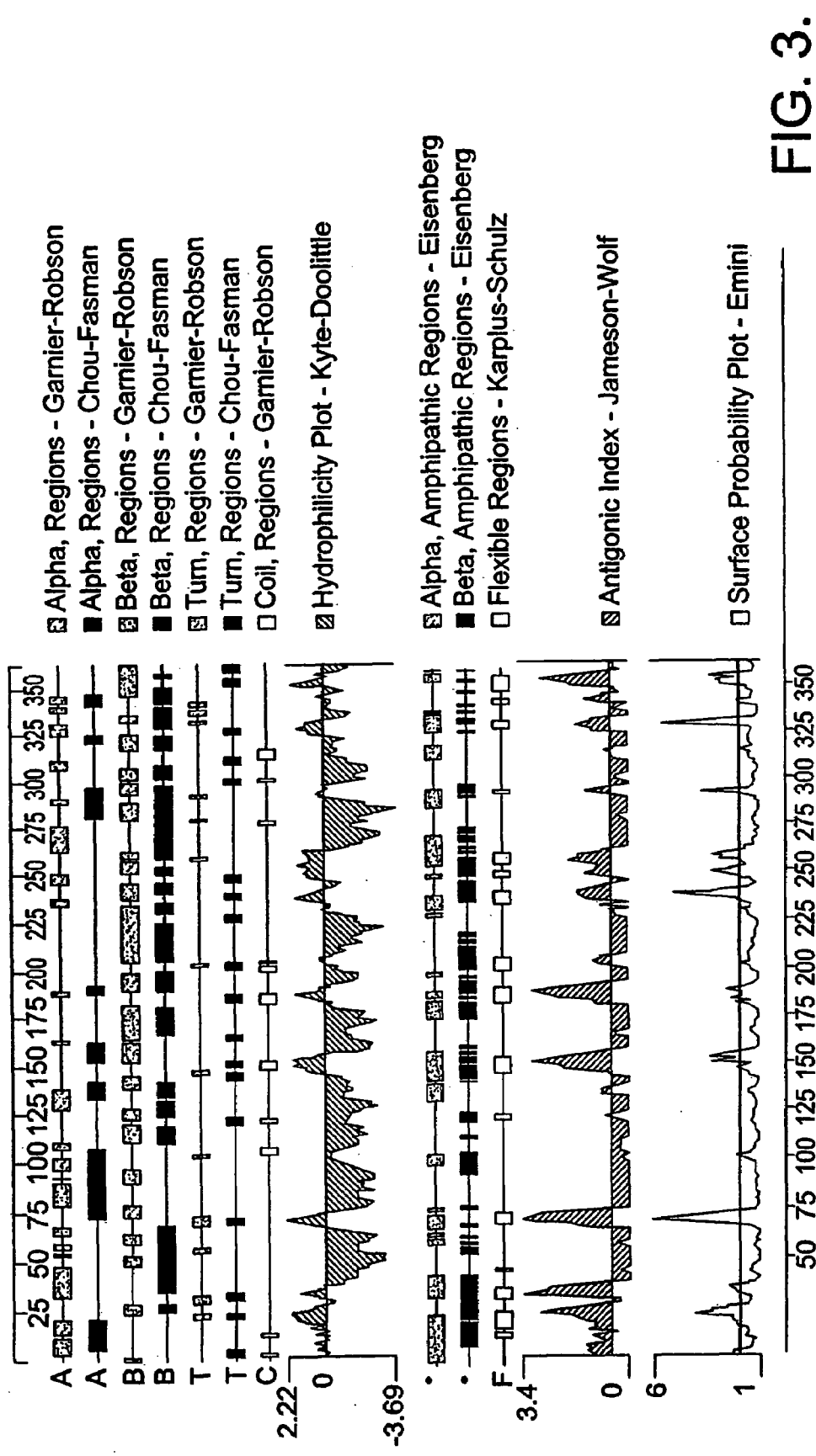

FIG. 3 shows an analysis of the human 14273 amino acid sequence: αβturn and coil regions; hydrophilicity; amphipathic regions; flexible regions; antigenic index; and surface probability plot.

FIG. 4 shows a human 14273 receptor hydrophobicity plot, showing the seven transmembrane segments. (FIh14237: SEQ ID NO: 1)

FIG. 5 shows an analysis of the human 14273 open reading frame for amino acids corresponding to specific functional sites. Glycosylation sites are found from about amino acids 21-24 and 322-325 of SEQ ID NO:1. A cyclic AMP- and cyclic GMP-dependent protein kinase phosphorylation site is found at about amino acids 239-242 of SEQ ID NO:1. A protein kinase C phosphorylation site is found from about amino acids 237-239 and 350-352 of SEQ ID NO:1. A casein kinase II phosphorylation site is found from about amino acids 256-259 of SEQ ID NO:1. N-myristoylation sites are found from about amino acids 57-62, 72-77, and 343-348 of SEQ ID NO:1. (SEQ ID NO: 6, SEQ ID NO: 7, and SEQ ID NO: 8, respectively). An amidation site is found at about amino acids 150-153 of SEQ ID NO:1. A leucine zipper pattern is shown at about amino acids 106-127 of SEQ ID NO:1(SEQ ID NO:9). In addition, amino acids corresponding in position to the GPCR signature and containing the invariant arginine are found in the sequence ERM at amino acids 135-137 of SEQ ID NO:1.

FIG. 6 shows human 14273 receptor transmembrane segments predicted by Memsat (A) Predicted segments for the presumed unprocessed peptide (B) Transmembrane segments for the presumed mature peptide. Numbering for the presumed mature peptide has been adjusted for the removal of the first 36 amino acids. (FIh14237: SEQ ID NO: 1; FIh14273 mature; anino acids 37-361 of SEQ ID NO:1)

FIGS. 7A-7B show the murine ortholog of 14273 nucleotide sequence (SEQ ID NO:5) and the deduced 14273 amino acid sequence (SEQ ID NO:4). It is predicted that amino acids 1-45 of SEQ ID NO:4 constitute the amino terminal extracellular domain, amino acids 46-321 of SEQ ID NO:4 constitute the region spanning the transmembrane domain, and amino acids 322-361 of SEQ ID NO:4 constitute the carboxy terminal intracellular domain. The transmembrane domain contains seven transmembrane segments, three extracellular loops and three intracellular loops. The transmembrane segments are found from about amino acid 96 to about amino acid 66, from about amino acid 77 to about amino acid 98, from about amino acid 113 to about amino acid 134, from about amino acid 156 to about amino acid 177, from about amino acid 209 to about amino acid 227, from about amino acid 266 to about amino acid 289, and from about amino acid 297 to about amino acid 321 of SEQ ID NO:4. Within the region spanning the entire transmembrane domain are three intracellular and three extracellular loops. The three intracellular loops are found from about amino acid 67 to about amino acid 76, from about amino acid 135 to about amino acid 155, and from about amino acid 228 to about amino acid 265 of SEQ ID NO:4. The three extracellular loops are found at from about amino acid 99 to about amino acid 112, from about amino acid 178 to about amino acid 208, and from about amino acid 290 to about amino acid 296 of SEQ ID NO:4.

The transmembrane domain includes a sequence, ERM, corresponding to the GPCR signal transduction signature, DRY, at residues 135-137 of SEQ ID NO:4. The sequence includes an arginine at residue 136 of SEQ ID NO:4, an invariant amino acid in GPCRs.

FIG. 8 shows a comparison of the murine 14273 receptor against the Prosite data base of protein patterns, specifically showing a high score against the seven transmembrane segment rhodopsin superfamily (SEQ ID NO:3). The underlined area shows a sequence corresponding to the GPCR signature, and specifically the position of an arginine residue, conserved in GPCRs. The most commonly conserved sequence is an aspartate, arginine, tyrosine (DRY) triplet. DRY is implicated in signal transduction. Arginine is invariant. Aspartate is conservatively placed in several GPCRs. In the present case, the arginine is found in the sequence ERM, which matches the position of DRY or invariant arginine in GPCRs of the rhodopsin superfamily of receptors.

Figure 9:
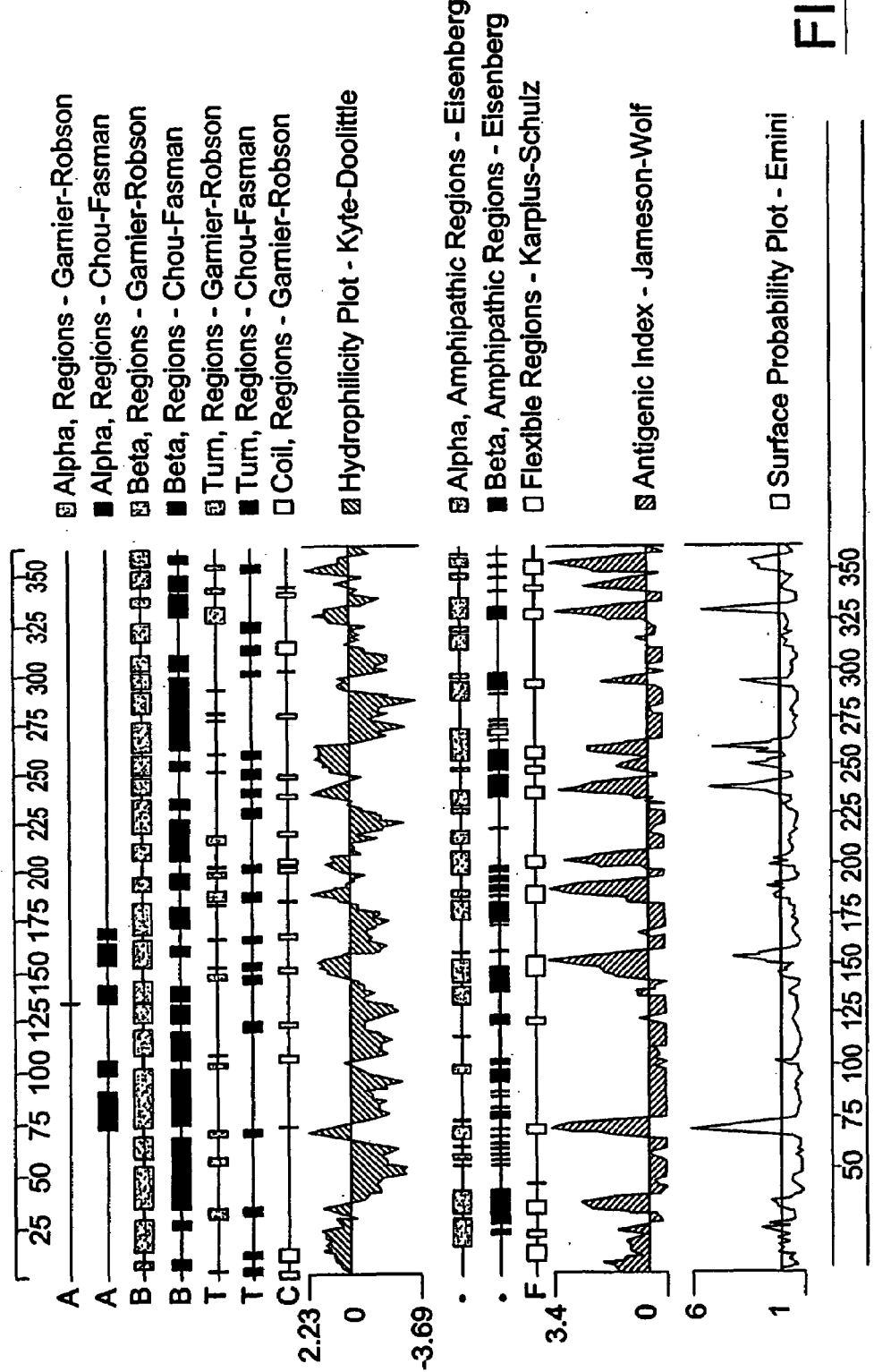

FIG. 9 shows an analysis of the murine 14273 amino acid sequence: αβturn and coil regions; hydrophilicity; amphipathic regions; flexible regions; antigenic index; and surface probability plot.

FIG. 10 shows a murine 14273 receptor hydrophobicity plot, showing the seven transmembrane segments. (14273m: SEQ ID NO:4)

FIG. 11 shows an analysis of the murine 14273 open reading frame for amino acids corresponding to specific functional sites. Glycosylation sites are found from about amino acids 21-24 and 322-325 of SEQ ID NO:4. A cyclic AMP- and cyclic GMP-dependent protein kinase phosphorylation site is found at about amino acids 239-242 of SEQ ID NO:4. A protein kinase C phosphorylation site is found from about amino acids 237-239 and 350-352 of SEQ ID NO:4. Casein kinase II phosphorylation sites are found from about amino acids 40-43 and 256-259 of SEQ ID NO:4. N-myristoylation sites are found from about amino acids 57-62, 72-77, and 343-348 of SEQ ID NO:4. An amidation site is found at about amino acids 150-153 of SEQ ID NO:4. A leucine zipper pattern is shown at about amino acids 106-127 of SEQ ID NO:4. In addition, amino acids corresponding in position to the GPCR signature and containing the invariant arginine are found in the sequence ERM at amino acids 135-137 of SEQ ID NO:4. A glycosaminoglycan attachment site is found at about amino acids 148-151 of SEQ ID NO:4.

FIG. 12 shows murine 14273 receptor transmembrane segments predicted by Memsat (A) predicted segments for the presumed unprocessed peptide (b) transmembrane segment for the presumed mature peptide. Numbering for the presumed mature peptide has been adjusted for the removal of the first 36 amino acids.

DETAILED DESCRIPTION OF THE INVENTION

Receptor Function/Signal Pathway

The 14273 receptor protein is a GPCR that participates in signaling pathways. As used herein, a "signaling pathway" refers to the modulation (e.g., stimulation or inhibition) of a cellular function/activity upon the binding of a ligand to the GPCR (14273 protein). Examples of such functions include mobilization of intracellular molecules that participate in a signal transduction pathway, e.g., phosphatidylinositol 4,5-bisphosphate ($PIP_2$), inositol 1,4,5-triphosphate ($IP_3$) and adenylate cyclase; polarization of the plasma membrane; production or secretion of molecules; alteration in the structure of a cellular component; cell proliferation, e.g., synthesis of DNA; cell migration; cell differentiation; and cell survival. Since the 14273 receptor protein is expressed in brain, heart, skeletal muscle, thymus, prostate, uterus and placenta, cells participating in a 14273 receptor protein signaling pathway include, but are not limited to, cells derived from these tissues.

The response mediated by the receptor protein depends on the type of cell. For example, in some cells, binding of a ligand to the receptor protein may stimulate an activity such as release of compounds, gating of a channel, cellular adhesion, migration, differentiation, etc., through phosphatidylinositol or cyclic AMP metabolism and turnover while in other cells, the binding of the ligand will produce a different result. Regardless of the cellular activity/response modulated by the receptor protein, it is universal that the protein is a GPCR and interacts with G proteins to produce one or more secondary signals, in a variety of intracellular signal transduction pathways, e.g., through phosphatidylinositol or cyclic AMP metabolism and turnover, in a cell.

As used herein, "phosphatidylinositol turnover and metabolism" refers to the molecules involved in the turnover and metabolism of phosphatidylinositol 4,5-bisphosphate ($PIP_2$) as well as to the activities of these molecules. $PIP_2$ is a phospholipid found in the cytosolic leaflet of the plasma membrane. Binding of ligand to the receptor activates, in some cells, the plasma-membrane enzyme phospholipase C that in turn can hydrolyze $PIP_2$ to produce 1,2-diacylglycerol (DAG) and inositol 1,4,5-triphosphate ($IP_3$). Once formed $IP_3$ can diffuse to the endoplasmic reticulum surface where it can bind an $IP_3$ receptor, e.g., a calcium channel protein containing an $IP_3$ binding site. $IP_3$ binding can induce opening of the channel, allowing calcium ions to be released into the cytoplasm. $IP_3$ can also be phosphorylated by a specific kinase to form inositol 1,3,4,5-tetraphosphate ($IP_4$), a molecule which can cause calcium entry into the cytoplasm from the extracellular medium. $IP_3$ and $IP_4$ can subsequently be hydrolyzed very rapidly to the inactive products inositol 1,4-biphosphate ($IP_2$) and inositol 1,3,4-triphosphate, respectively. These inactive products can be recycled by the cell to synthesize $PIP_2$. The other second messenger produced by the hydrolysis of $PIP_2$, namely 1,2-diacylglycerol (DAG), remains in the cell membrane where it can serve to activate the enzyme protein kinase C. Protein kinase C is usually found soluble in the cytoplasm of the cell, but upon an increase in the intracellular calcium concentration, this enzyme can move to the plasma membrane where it can be activated by DAG. The activation of protein kinase C in different cells results in various cellular responses such as the phosphorylation of glycogen synthase, or the phosphorylation of various transcription factors, e.g., NF-kB. The language "phosphatidylinositol activity", as used herein, refers to an activity of $PIP_2$ or one of its metabolites.

Another signaling pathway in which the receptor may participate is the cAMP turnover pathway. As used herein, "cyclic AMP turnover and metabolism" refers to the molecules involved in the turnover and metabolism of cyclic AMP (cAMP) as well as to the activities of these molecules. Cyclic AMP is a second messenger produced in response to ligand-induced stimulation of certain G protein coupled receptors. In the cAMP signaling pathway, binding of a ligand to a GPCR can lead to the activation of the enzyme adenyl cyclase, which catalyzes the synthesis of cAMP. The newly synthesized cAMP can in turn activate a cAMP-dependent protein kinase. This activated kinase can phosphorylate a voltage-gated potassium channel protein, or an associated protein, and lead to the inability of the potassium channel to open during an action potential. The inability of the potassium channel to open results in a decrease in the outward flow of potassium, which normally repolarizes the membrane of a neuron, leading to prolonged membrane depolarization.

Polypeptides

The invention is based on the discovery of a novel G-coupled protein receptor. Specifically, an expressed sequence tag (EST) was selected based on homology to G-protein-coupled receptor sequences. This EST was used to design primers based on sequences that it contains and used to identify a cDNA from a human fetal brain cDNA library. Positive clones were sequenced and the overlapping fragments were assembled. Analysis of the assembled sequence revealed that the cloned cDNA molecule encodes a G-protein coupled receptor. The amino acid sequence of this receptor shows homology with galanin receptors, chemokine receptors and somatostatin.

Galanin is a small neuroendocrine peptide with 29 amino acids. The major biological functions are to promote growth hormone release, inhibit glucose-induced insulin release, impair cognitive function, stimulate feeding behavior, and regulate motility in the gastrointestinal tract. For background and functions of galanin see U.S. Pat. No. 5,756,460. See, also, WO 98/15570 for teaching regarding galanin and galanin receptor function. These documents are herein incorporated by reference for these teachings.

RH linkage analysis was performed using the Map Manager QTb 23 software package. The 14273 receptor was found to map to human chromosome 10, 10.0 cR3000 telomeric to the Whitehead Institute framework marker D10S583, and 13.3 cR3000 centromeric of the Whitehead framework marker D10S185. Two point LOD scores for linkage were 15.5 for D10S583 and 14.4 for D10S185. This region corresponds to a cytogenetic location of 10q23.1-23.3. This location places it in close proximity to the region defined as CMD1C, cardiomyopathy, dilated, 1C. Bowles, K. R., et al. (*J. Clin. Invest.* 98:1344-1360 (1996)) reported the discovery of the third locus for a pure autosomal dominant familial dilated cardiomyopathy on chromosome 10q21-q23. In addition to the familial dilated cardiomyopathy, the family studied in this report had associated mitral valve prolapse and mitral regurgitation. It has been demonstrated (Sanyal et al., *Pediatrics* 63:116-122 (1979)) that these result from degeneration of the posterior papillary muscles or ventricular myocardium in patients, causing instability of the mitral apparatus and secondary prolapse. Since familial dilated cardiomyopathy is a primary disorder of the ventricular myocardium due to a genetically-determined protein defect (such as a cytoskeletal protein), which would also involve the papillary muscles, the dilated cardiomyopathy-causing protein defect could also be the underlying cause of the associated mitral valve prolapse.

Dilated cardiomyopathy is the most common form of cardiomyopathy. Many causes have been described but most commonly the disease is considered idiopathic. Patients generally present signs and symptoms of congestive heart failure. Diagnosis generally depends on evidence of ventricular dilatation and dysfunction. Premature death, especially cardiac death from ventricular arrhythmias or ischemia is common. In a significant number of cases, a familial inheritance pattern is observed with autosomal dominant transmission being the most common form of transmission. The underlying genetic defect was not known. As discussed above, a form of familial dilated cardiomyopathy was mapped to the long arm of chromosome 10 (10q21-10q23) in one family in which the phenotype was a pure dilated cardiomyopathy with mitral valve prolapse (cite above).

In mapping the 14273 receptor to a specific genetic location corresponding to 10q23.1-23.3, the inventors have correlated the receptor that is the subject of the invention to the region defined as cardiomyopathy dilated 1C. This provides the first association of a specific gene with this locus, providing the basis for a genetic lesion associated with dilated cardiomyopathy.

The expression of the 14273 receptor is induced at the RNA level in hypertrophic cardiac myocytes in diseased human hearts. This includes, but is not limited to, both dilated and ischemic hearts. In addition, transgenic mice overexpressing the 14273 receptor developed cardiomyocyte hypertrophy, many of these mice dying from heart failure. In several independently constructed series of transgenic animals in which the 14273 receptor can be specifically overexpressed in cardiomyocytes, heart histopathology shows biventricular dilatation, cardiomyocyte hypertrophy, atrial thrombi, and interstitial fibrosis. A significant number of affected mice show a heart:body weight ratio significantly increased. In transgenic mice in which the receptor is expressed and in which the hypertrophic phenotype is developed, receptor mRNA and protein levels can be correlated with the severity of the phenotype. In one series, the ratios are approximately 1.5-2.7. Enlargement of atrium, ventricle thrombosis in the atrium, edema in the chest, and breathing difficulties, were observed. In a pressure overload model (rat), cardiac hypertrophy was induced by banding of the aorta. Development of the hypertrophic phenotype was correlated with induction of the 14273 receptor at the mRNA level by 22 weeks after banding. Accordingly, the inventors have discovered a novel gene that can produce cardiovascular disease as well as serve as a target for treatment and diagnosis.

The invention thus relates to a novel GPCR having the deduced amino acid sequence shown in FIG. 1 (SEQ ID NO:1) or having the amino acid sequence encoded by the deposited cDNA, ATCC No. PTA-1143. The invention also relates to the mouse ortholog corresponding to the novel human GPCR having the deduced amino acid sequence shown in FIG. 7 (SEQ ID NO:4) or having the amino acid sequence encoded by the deposited cDNA, ATCC No. PTA-1143.

The deposit will be maintained under the terms of the Budapest Treaty on the International Recognition of the Deposit of Microorganisms. The deposit is provided as a convenience to those of skill in the art and is not an admission that a deposit is required under 35 U.S.C. § 112. The deposited sequence, as well as the polypeptide encoded by the sequence, is incorporated herein by reference and controls in the event of any conflict, such as a sequencing error, with description in this application.

Much of the detailed description is directed specifically to the human receptor polypeptide or nucleic acid. However, it is understood that this description applies also to the murine ortholog with the proviso that specific regions, such as segments, domains, fragments, antigenic sites, and the like, would be modified according to the sequence details and domain analysis provided for the mouse ortholog in the figures herein. Accordingly, where the description refers to the 14273 receptor generically, this description refers to both the murine and human receptor. Where the description would necessarily be limited to the human receptor (as for example, in designating specific fragments, segments, or domains), to ascertain the corresponding details pertaining to the murine ortholog, FIGS. 7A-12 should be consulted.

The "14273 receptor polypeptide" or "14273 receptor protein" refers to the polypeptide in SEQ ID NO:1 or SEQ ID NO:4 or encoded by the deposited cDNA. The term "receptor protein" or "receptor polypeptide", however, further includes the numerous variants described herein, as well as fragments derived from the full length 14273 polypeptide and variants.

The present invention thus provides an isolated or purified 14273 receptor polypeptide and variants and fragments thereof.

The human 14273 polypeptide is a 361 residue protein exhibiting three main structural domains. The amino terminal extracellular domain is identified to be within residues 1 to about 45 in SEQ ID NO:1. The transmembrane domain is identified to be within residues from about 46 to about 321 in SEQ ID NO:1. The carboxy terminal intracellular domain is identified to be within residues from about 322 to 361 in SEQ ID NO:1. The transmembrane domain contains seven segments that span the membrane. The transmembrane segments are found from about amino acid 46 to about amino acid 66, from about amino acid 75 to about amino acid 98, from about amino acid 113 to about amino acid 134, from about amino acid 156 to about amino acid 177, from about amino acid 209 to about amino acid 227, from about amino acid 266 to about amino acid 289, and from about amino acid 297 to about amino acid 321 of SEQ ID NO:1. Within the region spanning the entire transmembrane domain are three intracellular and three extracellular loops. The three intracellular loops are found from about amino acid 67 to about amino acid 74, from about amino acid 135 to about amino acid 155, and from about amino acid 228 to about amino acid 265 of SEQ ID NO:1. The three extracellular loops are found at from about amino acid 99 to about amino acid 112, from about amino acid 178 to about amino acid 208, and from about amino acid 290 to about amino acid 296 of SEQ ID NO:1.

The transmembrane domain includes a GPCR signal transduction signature, ERM, at residues 135-137 of SEQ ID NO:1. The sequence includes an arginine at residue 136 of SEQ ID NO:1, an invariant amino acid in GPCRs.

Based on a BLAST search, highest homology was shown to galanin receptors. Galanin receptors include the GAL I, GAL II, and GAL III receptors. Significant homology was also found with chemokine receptors and somatostatin receptors.

As used herein, a polypeptide is said to be "isolated" or "purified" when it is substantially free of cellular material when it is isolated from recombinant and non-recombinant cells, or free of chemical precursors or other chemicals when it is chemically synthesized. A polypeptide, however, can be joined to another polypeptide with which it is not normally associated in a cell and still be considered "isolated" or "purified."

The receptor polypeptides can be purified to homogeneity. It is understood, however, that preparations in which the polypeptide is not purified to homogeneity are useful and considered to contain an isolated form of the polypeptide. The critical feature is that the preparation allows for the desired function of the polypeptide, even in the presence of considerable amounts of other components. Thus, the invention encompasses various degrees of purity.

In one embodiment, the language "substantially free of cellular material" includes preparations of the receptor polypeptide having less than about 30% (by dry weight) other proteins (i.e., contaminating protein), less than about 20% other proteins, less than about 10% other proteins, or less than about 5% other proteins. When the receptor polypeptide is recombinantly produced, it can also be substantially free of culture medium, i.e., culture medium represents less than about 20%, less than about 10%, or less than about 5% of the volume of the protein preparation.

The language "substantially free of chemical precursors or other chemicals" includes preparations of the receptor polypeptide in which it is separated from chemical precursors or other chemicals that are involved in its synthesis. In one embodiment, the language "substantially free of chemical precursors or other chemicals" includes preparations of the polypeptide having less than about 30% (by dry weight) chemical precursors or other chemicals, less than about 20% chemical precursors or other chemicals, less than about 10% chemical precursors or other chemicals, or less than about 5% chemical precursors or other chemicals.

In one embodiment, the receptor polypeptide comprises the amino acid sequence shown in SEQ ID NO: 1 or SEQ ID NO:4. However, the invention also encompasses sequence variants. Variants include a substantially homologous protein encoded by the same genetic locus in an organism, i.e., an allelic variant. Variants also encompass proteins derived from other genetic loci in an organism, but having substantial homology to the 14273 receptor protein of SEQ ID NO:1 or SEQ ID NO:4. Variants also include proteins substantially homologous to the 14273 receptor protein but derived from another organism, i.e., an ortholog. Variants also include proteins that are substantially homologous to the 14273 receptor protein that are produced by chemical synthesis. Variants also include proteins that are substantially homologous to the 14273 receptor protein that are produced by recombinant methods. It is understood, however, that variants exclude any amino acid sequences disclosed prior to the invention.

As used herein, two proteins (or a region of the proteins) are substantially homologous when the amino acid sequences are at least about 50-55%, 55-60%, typically at least about 70-75%, more typically at least about 80-85%, and most typically at least about 90-95% or more homologous. A substantially homologous amino acid sequence, according to the present invention, will be encoded by a nucleic acid sequence hybridizing to the nucleic acid sequence, or portion thereof, of the sequence shown in SEQ ID NO:2 or SEQ ID NO:5 under stringent conditions as more fully described below.

To determine the percent identity of two amino acid sequences or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, the length of a reference sequence aligned for comparison purposes is at least 30%, preferably at least 40%, more preferably at least 50%, even more preferably at least 60%, and even more preferably at least 70%, 80%, or 90% of the length of the reference sequence (e.g., when aligning a second sequence to the amino acid sequences herein having 100 amino acid residues, at least 140, preferably at least 180, more preferably at least 250, even more preferably at least 290, and even more preferably at least 320 amino acid residues are aligned). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The invention also encompasses polypeptides having a lower degree of identity but having sufficient similarity so as to perform one or more of the same functions performed by the 14273 polypeptide. Similarity is determined by conserved amino acid substitution. Such substitutions are those that substitute a given amino acid in a polypeptide by another amino acid of like characteristics. Conservative substitutions are likely to be phenotypically silent. Typically seen as conservative substitutions are the replacements, one for another, among the aliphatic amino acids Ala, Val, Leu, and Ile; interchange of the hydroxyl residues Ser and Thr, exchange of the acidic residues Asp and Glu, substitution between the amide residues Asn and Gln, exchange of the basic residues Lys and Arg and replacements among the aromatic residues Phe, Tyr. Guidance concerning which amino acid changes are likely to be phenotypically silent are found in Bowie et al., *Science* 247:1306-1310 (1990).

TABLE 1

Conservative Amino Acid Substitutions.

| | |
|---|---|
| Aromatic | Phenylalanine |
| | Tryptophan |
| | Tyrosine |
| Hydrophobic | Leucine |
| | Isoleucine |
| | Valine |
| Polar | Glutamine |
| | Asparagine |
| Basic | Arginine |
| | Lysine |
| | Histidine |
| Acidic | Aspartic Acid |
| | Glutamic Acid |
| Small | Alanine |
| | Serine |
| | Threonine |
| | Methionine |
| | Glycine |

The comparison of sequences and determination of percent identity and similarity between two sequences can be accomplished using a mathematical algorithm. (*Computational Molecular Biology*, Lesk, A. M., ed., Oxford University Press, New York, 1988; *Biocomputing: Informatics and Genome Projects*, Smith, D. W., ed., Academic Press, New York, 1993; *Computer Analysis of Sequence Data, Part* 1, Griffin, A. M., and Griffin, H. G., eds., Humana Press, New Jersey, 1994; *Sequence Analysis in Molecular Biology*, von Heinje, G., Academic Press, 1987; and *Sequence Analysis Primer*, Gribskov, M. and Devereux, J., eds., M Stockton Press, New York, 1991). In a preferred embodiment, the percent identity between two amino acid sequences is determined using the Needleman and Wunsch (*J. Mol. Biol.* (48): 444-453 (1970)) algorithm which has been incorporated into the GAP program in the GCG software package, using either a Blossom 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (Devereux, J., et al., *Nucleic Acids Res.* 12(1):387 (1984)), using a NWSgapdna.CMP matrix and a gap weight of 40, 50, 60, 70, or 80 and a length weight of 1, 2, 3, 4, 5, or 6. In another embodiment, the percent identity between two amino acid or nucleotide sequences is determined using the algorithm of E. Meyers and W. Miller (CABIOS, 4:11-17 (1989)) which has been incorporated into the ALIGN program (version 2.0), using a PAM120 weight residue table, a gap length penalty of 12 and a gap penalty of 4.

The nucleic acid and protein sequences of the present invention can further be used as a "query sequence" to perform a search against public databases to, for example, identify other family members or related sequences. Such searches can be performed using the NBLAST and XBLAST programs (version 2.0) of Altschul, et al. (1990) *J. Mol. Biol.* 215:403-10. BLAST nucleotide searches can be performed with the NBLAST program, score=100, wordlength=12 to obtain nucleotide sequences homologous to the nucleic acid molecules of the invention. BLAST protein searches can be performed with the XBLAST program, score=50, wordlength=3 to obtain amino acid sequences homologous to the proteins of the invention. To obtain gapped alignments for comparison purposes, Gapped BLAST can be utilized as described in Altschul et al., (1997) *Nucleic Acids Res.* 25(17): 3389-3402. When utilizing BLAST and Gapped BLAST programs, the default parameters of the respective programs (e.g., XBLAST and NBLAST) can be used.

A variant polypeptide can differ in amino acid sequence by one or more substitutions, deletions, insertions, inversions, fusions, and truncations or a combination of any of these.

Variant polypeptides can be fully functional or can lack function in one or more activities. Thus, in the present case, variations can affect the function, for example, of one or more of the regions corresponding to ligand binding, membrane association, G-protein binding and signal transduction.

Fully functional variants typically contain only conservative variation or variation in non-critical residues or in non-critical regions. Functional variants can also contain substitution of similar amino acids which result in no change or an insignificant change in function. Alternatively, such substitutions may positively or negatively affect function to some degree.

Non-functional variants typically contain one or more non-conservative amino acid substitutions, deletions, insertions, inversions, or truncation or a substitution, insertion, inversion, or deletion in a critical residue or critical region.

As indicated, variants can be naturally-occurring or can be made by recombinant means or chemical synthesis to provide useful and novel characteristics for the receptor polypeptide. This includes preventing immunogenicity from pharmaceutical formulations by preventing protein aggregation.

Useful variations further include alteration of ligand binding characteristics. For example, one embodiment involves a variation at the binding site that results in binding but not release, or slower release, of ligand. A further useful variation at the same sites can result in a higher affinity for ligand. Useful variations also include changes that provide for affinity for another ligand. Another useful variation includes one that allows binding but which prevents activation by the ligand. Another useful variation includes variation in the transmembrane G-protein-binding/signal transduction domain that provides for reduced or increased binding by the appropriate G-protein or for binding by a different G-protein than the one with which the receptor is normally associated. Another useful variation provides a fusion protein in which one or more domains or subregions is operationally fused to one or more domains or subregions from another G-protein coupled receptor.

Amino acids that are essential for function can be identified by methods known in the art, such as site-directed mutagenesis or alanine-scanning mutagenesis (Cunningham et al., *Science* 244:1081-1085 (1989)). The latter procedure introduces single alanine mutations at every residue in the molecule. The resulting mutant molecules are then tested for biological activity such as receptor binding or in vitro, or in vitro proliferative activity. Sites that are critical for ligand-receptor binding can also be determined by structural analysis such as crystallization, nuclear magnetic resonance or photoaffinity labeling (Smith et al., *J. Mol. Biol.* 224:899-904 (1992); de Vos et al. *Science* 255:306-312 (1992)).

Substantial homology can be to the entire nucleic acid or amino acid sequence or to fragments of these sequences.

The invention thus also includes polypeptide fragments of the 14273 receptor protein. Fragments can be derived from the amino acid sequence shown in SEQ ID NO:1 or SEQ ID NO:4. However, the invention also encompasses fragments of the variants of the 14273 receptor protein as described herein.

As used herein, a fragment comprises at least 6 contiguous amino acids from amino acid 1-127 of SEQ ID NO:1 or SEQ ID NO:4, at least 9 amino acids from amino acid 1 to about amino acid 184 of SEQ ID NO:1 or SEQ ID NO:4, greater than 10 amino acids from amino acid 1 to about amino acid 210 of SEQ ID NO:1 or SEQ ID NO:4, and fragments greater than 32 amino acids from amino acid 1 to about amino acid 291 of SEQ ID NO:1 or SEQ ID NO:4. Specific fragments also include fragments greater than those found from amino acid 123-132, 134-141, 162-167, 177-186, 203-237, 238-242, 244-259, 261-292, 295-323, 332-337, 339-345, and 347-351 of SEQ ID NO:1 or SEQ ID NO:4.

Fragments can retain one or more of the biological activities of the protein, for example the ability to bind to a G-protein or ligand. Fragments can also be useful as an immunogen to generate receptor antibodies.

Biologically active fragments can comprise a domain or motif, e.g., an extracellular or intracellular domain or loop, one or more transmembrane segments, or parts thereof, G-protein binding site, or GPCR signature, glycosylation, myristoylation, amidation, and phosphorylation sites, and sites showing a leucine zipper pattern L [a-z] {6} L [a-z] {6} L[a-z] {6} L sites. Such peptides can be, for example, 6, 10, 15, 20, 30, 35, 36, 37, 38, 39, 40, 50, 100 or more amino acids in length.

Possible fragments of the human receptor include, but are not limited to: 1) soluble peptides comprising the entire amino terminal extracellular domain about amino acid 1 to about amino acid 45 of SEQ ID NO:1, or parts thereof; 2) peptides comprising the entire carboxy terminal intracellular domain from about amino acid 322 to amino acid 361 of SEQ ID NO:1, or parts thereof; 3) peptides comprising the region spanning the entire transmembrane domain from about amino acid 46 to about amino acid 321 of SEQ ID NO:1, or parts thereof; 4) any of the specific transmembrane segments, or parts thereof, from about amino acid 46 to about amino acid 66, from about amino acid 75 to about amino acid 98, from about amino acid 113 to about amino acid 134, from about amino acid 156 to about amino acid 177, from about amino acid 209 to about amino acid 227, from about amino acid 266 to about amino acid 289, and from about amino acid 297 to about amino acid 321 of SEQ ID NO:1; 5) any of the three intracellular or three extracellular loops, or parts thereof, from about amino acid 67 to about amino acid 74, from about amino acid 135 to about amino acid 155, from about amino acid 228 to about amino acid 265, from about amino acid 99 to about amino acid 112, from about amino acid 178 to about amino acid 208, and from about amino acid 290 to about amino acid 296 of SEQ ID NO:1. Fragments further include combinations of the above fragments, such as an amino terminal domain combined with one or more transmembrane segments and the attendant extra or intracellular loops or one or more transmembrane segments, and the attendant intra or extracellular loops, plus the carboxy terminal domain. Thus, any of the above fragments can be combined. Other fragments include the mature protein from about amino acid 37 to 361 of SEQ ID NO:1. Other fragments contain the various functional sites described herein and a sequence containing the GPCR signature sequence. Fragments, for example, can extend in one or both directions from the functional site to encompass 5, 10, 15, 20, 30, 40, 50, or up to 100 amino acids. Further, fragments can include sub-fragments of the specific domains mentioned above, which sub-fragments retain the function of the domain from which they are derived.

Fragments also include antigenic fragments and specifically those shown to have a high antigenic index in FIGS. 3 and 9.

Accordingly, possible fragments include fragments defining a ligand-binding site, fragments defining a glycosylation, amidation, phosphorylation, or myristoylation site, fragments defining membrane association, fragments defining interaction with G proteins and signal transduction, and fragments defining leucine zipper sites. By this is intended a discrete fragment that provides the relevant function or allows the relevant function to be identified. In a preferred embodiment, the fragment contains the ligand-binding site.

The invention also provides fragments with immunogenic properties. These contain an epitope-bearing portion of the 14273 receptor protein and variants. These epitope-bearing peptides are useful to raise antibodies that bind specifically to a receptor polypeptide or region or fragment. These peptides can contain at least 6, 12, at least 14, or between at least about 15 to about 30 amino acids.

Non-limiting examples of antigenic polypeptides that can be used to generate antibodies include peptides derived from the amino terminal extracellular domain or any of the extracellular loops. Regions having a high antigenicity index are shown in FIGS. 3 and 9. However, intracellularly-made antibodies ("intrabodies") are also encompassed, which would recognize intracellular receptor peptide regions.

The fragments to which the invention pertains, however, are not to be construed as encompassing fragments that may be disclosed prior to the present invention.

The receptor polypeptides (including variants and fragments which may have been disclosed prior to the present invention) are useful for biological assays related to GPCRs. Such assays involve any of the known GPCR functions or activities or properties useful for diagnosis and treatment of GPCR-related conditions.

The epitope-bearing receptor and polypeptides may be produced by any conventional means (Houghten, R. A., *Proc. Natl. Acad. Sci. USA* 82:5131-5135 (1985)). Simultaneous multiple peptide synthesis is described in U.S. Pat. No. 4,631,211.

Fragments can be discrete (not fused to other amino acids or polypeptides) or can be within a larger polypeptide. Further, several fragments can be comprised within a single larger polypeptide. In one embodiment a fragment designed for expression in a host can have heterologous pre- and pro-polypeptide regions fused to the amino terminus of the receptor fragment and an additional region fused to the carboxyl terminus of the fragment.

The invention thus provides chimeric or fusion proteins. These comprise a receptor protein operatively linked to a heterologous protein having an amino acid sequence not substantially homologous to the receptor protein. "Operatively linked" indicates that the receptor protein and the heterologous protein are fused in-frame. The heterologous protein can be fused to the N-terminus or C-terminus of the receptor protein.

In one embodiment the fusion protein does not affect receptor function per se. For example, the fusion protein can be a GST-fusion protein in which the receptor sequences are fused to the C-terminus of the GST sequences. Other types of fusion proteins include, but are not limited to, enzymatic fusion proteins, for example beta-galactosidase fusions, yeast two-hybrid GAL fusions, poly-His fusions and Ig fusions. Such fusion proteins, particularly poly-His fusions, can facilitate the purification of recombinant receptor protein. In certain host cells (e.g., mammalian host cells), expression and/or secretion of a protein can be increased by using a heterologous signal sequence. Therefore, in another embodiment, the fusion protein contains a heterologous signal sequence at its N-terminus.

EP-A-O 464 533 discloses fusion proteins comprising various portions of immunoglobulin constant regions. The Fc is useful in therapy and diagnosis and thus results, for example, in improved pharmacokinetic properties (EP-A 0232 262). In drug discovery, for example, human proteins have been fused with Fc portions for the purpose of high-throughput screening assays to identify antagonists. Bennett et al. (*J. Mol. Recog.* 8:52-58 (1995)) and Johanson et al. (*J. Biol. Chem.* 270, 16:9459-9471 (1995)). Thus, this invention also encompasses soluble fusion proteins containing a receptor polypeptide and various portions of the constant regions of heavy or light chains of immunoglobulins of various subclass (IgG, IgM, IgA, IgE). Preferred as immunoglobulin is the constant part of the heavy chain of human IgG, particularly IgG1, where fusion takes place at the hinge region. For some uses it is desirable to remove the Fc after the fusion protein has been used for its intended purpose, for example when the fusion protein is to be used as antigen for immunizations. In a particular embodiment, the Fc part can be removed in a simple way by a cleavage sequence which is also incorporated and can be cleaved with factor Xa.

A chimeric or fusion protein can be produced by standard recombinant DNA techniques. For example, DNA fragments coding for the different protein sequences are ligated together in-frame in accordance with conventional techniques. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and re-amplified to generate a chimeric gene sequence (see Ausubel et al., *Current Protocols in Molecular Biology,* 1992). Moreover, many expression vectors are commercially available that already encode a fusion moiety (e.g., a GST protein). A receptor protein-encoding nucleic acid can be cloned into such an expression vector such that the fusion moiety is linked in-frame to the receptor protein.

Another form of fusion protein is one that directly affects receptor functions. Accordingly, a receptor polypeptide is encompassed by the present invention in which one or more of the receptor domains (or parts thereof) has been replaced by homologous domains (or parts thereof) from another G-protein coupled receptor or other type of receptor. Accordingly, various permutations are possible. The amino terminal extracellular domain, or subregion thereof (for example, ligand-binding), can be replaced with the domain or subregion from another ligand-binding receptor protein. Alternatively, the entire transmembrane domain or any of the seven segments or loops, or parts thereof, for example, G-protein-binding/signal transduction, can be replaced. Finally, the carboxy terminal intracellular domain or subregion can be replaced. Thus, chimeric receptors can be formed in which one or more of the native domains or subregions has been replaced.

The isolated receptor protein can be purified from cells that naturally express it, such as from fetal brain, heart, skeletal muscle, thymus, prostate, placenta, and uterus, where expression of the receptor has been detected, especially in heart and skeletal muscle, purified from cells that have been altered to express it (recombinant), or synthesized using known protein synthesis methods. Preferred embodiments include isolation from recombinant cardiomyocytes or from diseased cardiomyocytes overexpressing a normal receptor gene or expressing a receptor variant. Variants that are correlated with cardiovascular diseases can be isolated from affected tissues or from at-risk individuals. Alternatively, such variants can be produced by chemical synthesis or by site-directed mutagenesis.

In one embodiment, the protein is produced by recombinant DNA techniques. For example, a nucleic acid molecule encoding the receptor polypeptide is cloned into an expression vector, the vector is introduced into a host cell and the protein is expressed in the host cell. The protein can then be isolated from the cells by an appropriate purification scheme using standard protein purification techniques.

Polypeptides often contain amino acids other than the 20 amino acids commonly referred to as the 20 naturally-occurring amino acids. Further, many amino acids, including the terminal amino acids, may be modified by natural processes, such as processing and other post-translational modifications, or by chemical modification techniques well known in the art. Common modifications that occur naturally in polypeptides are described in basic texts, detailed monographs, and the research literature, and they are well known to those of skill in the art.

Accordingly, the polypeptides also encompass derivatives or analogs in which a substituted amino acid residue is not one encoded by the genetic code, in which a substituent group is included, in which the mature polypeptide is fused with another compound, such as a compound to increase the half-life of the polypeptide (for example, polyethylene glycol), or in which the additional amino acids are fused to the mature polypeptide, such as a leader or secretory sequence or a sequence for purification of the mature polypeptide or a pro-protein sequence.

Known modifications include, but are not limited to, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphatidylinositol, cross-linking, cyclization, disulfide bond formation, demethylation, formation of covalent crosslinks, formation of cystine, formation of pyroglutamate, formylation, gamma carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination.

Such modifications are well-known to those of skill in the art and have been described in great detail in the scientific literature. Several particularly common modifications, glycosylation, lipid attachment, sulfation, gamma-carboxylation of glutamic acid residues, hydroxylation and ADP-ribosylation, for instance, are described in most basic texts, such as *Proteins—Structure and Molecular Properties,* 2nd Ed., T. E. Creighton, W. H. Freeman and Company, New York (1993). Many detailed reviews are available on this subject, such as by Wold, F., *Posttranslational Covalent Modification of Proteins,* B. C. Johnson, Ed., Academic Press, New York 1-12 (1983); Seifter et al. (*Meth. Enzymol.* 182: 626-646 (1990)) and Rattan et al. (*Ann. N.Y. Acad. Sci.* 663:48-62 (1992)).

As is also well known, polypeptides are not always entirely linear. For instance, polypeptides may be branched as a result of ubiquitination, and they may be circular, with or without branching, generally as a result of post-translation events, including natural processing event and events brought about by human manipulation which do not occur naturally. Circular, branched and branched circular polypeptides may be synthesized by non-translational natural processes and by synthetic methods.

Modifications can occur anywhere in a polypeptide, including the peptide backbone, the amino acid side-chains and the amino or carboxyl termini. Blockage of the amino or carboxyl group in a polypeptide, or both, by a covalent modification, is common in naturally-occurring and synthetic polypeptides. For instance, the amino terminal residue of polypeptides made in *E. coli*, prior to proteolytic processing, almost invariably will be N-formylmethionine.

The modifications can be a function of how the protein is made. For recombinant polypeptides, for example, the modifications will be determined by the host cell posttranslational modification capacity and the modification signals in the polypeptide amino acid sequence. Accordingly, when glycosylation is desired, a polypeptide should be expressed in a glycosylating host, generally a eukaryotic cell. Insect cells often carry out the same posttranslational glycosylations as mammalian cells and, for this reason, insect cell expression systems have been developed to efficiently express mammalian proteins having native patterns of glycosylation. Similar considerations apply to other modifications.

The same type of modification may be present in the same or varying degree at several sites in a given polypeptide. Also, a given polypeptide may contain more than one type of modification.

Polypeptide Uses

Expression of the 14273 receptor has been associated by the inventors with cardiovascular diseases. mRNA screening of normal and diseased human tissues showed the induction of receptor mRNA in hypertrophic cardiac myocytes. This induction is associated with morphological change. In a transgenic mouse model in which the receptor is specifically overexpressed in cardiomyocytes, the overexpression results in cardiomyocyte enlargement. In several independently generated transgenic mouse models, the mice developed cardiomyocyte hypertrophy, many of these mice dying from heart failure. Histological analysis of hearts from these animals showed biventricular dilatation, cardiomyocyte hypertrophy, interstitial fibrosis and atrial thrombi. The heart:body weight ratio was increased. In one series the ratio ranged from approximately 1.5-2.7. Enlargement of the hearts, thrombosis in the atrium, edema in the chest, and breathing difficulties, were observed. Accordingly, any of the specific uses described herein include the context of cardiovascular diseases or a predisposition for developing cardiovascular diseases, for example, the cardiovascular diseases discussed herein as associated with receptor expression.

The receptor polypeptides are useful for producing antibodies specific for the 14273 receptor protein, regions, or fragments. Regions having a high antigenicity index score are shown in FIGS. 3 and 9. For example, modified receptor polypeptides isolated from diseased tissues can be used to prepare antibodies, which are then useful for screening for gene expression in diseased tissues in vitro or in vivo, modulating gene expression, and treating disorders associated with the receptor polypeptides, especially cardiovascular diseases. Modified receptor polypeptides prepared by chemical synthesis or by such techniques as site-directed mutagenesis, if found to be pertinent to a disorder such as cardiovascular diseases, can also be used to prepare antibodies for screening and modulation.

In one embodiment, an antibody was developed against a C-terminal antigenic segment (amino acids 348-361), DTS-VKRNDLSIISG. This antibody was successfully used to show the overexpression of the receptor in transgenic mice containing the receptor gene and specifically in cardiomyocytes. The antibody did not bind to control samples not containing and/or expressing the gene for the receptor.

The receptor polypeptides (including variants and fragments which may have been disclosed prior to the present invention) are useful for biological assays related to GPCRs. Such assays involve any of the known GPCR functions or activities or properties useful for diagnosis and treatment of GPCR-related conditions. Diseased tissue, such as cardiac tissue, skeletal muscle, uterus, thymus, and prostate, can be used to identify modified receptor polypeptides which then serve as a basis for diagnosis and for rational drug design.

The receptor polypeptides are also useful in drug screening assays, in cell-based or cell-free systems. Cell-based systems can be native, i.e., cells that normally express the receptor protein, as a biopsy or expanded in cell culture. In one embodiment, however, cell-based assays involve recombinant host cells expressing the receptor protein. Diseased tissue, specifically, diseased cardiac tissue (such as diseased heart), skeletal muscle, thymus, uterus, and prostate, are useful to screen for drugs that can be used in affecting the diseased tissue. Preferred cells include, but are not limited to, cardiac myocytes, and especially hypertrophic cardiac myocytes. The effect of the drug can be scored based on, among other things, morphological change.

Cardiomyocytes for drug screening assays can be normal or can be derived from patients having cardiovascular disease or having a predisposition to such disease. Accordingly, cardiomyocytes can be enlarged or derived from a patient having a tendency to produce such enlarged cardiomyocytes. These cardiomyocytes can thus be tested for agents that affect the biochemistry of the cardiomyocytes by affecting the receptor gene or gene product. These cardiomyocytes can be further modified by recombinant DNA techniques to add or delete copies of receptor gene sequences or to introduce altered sequences. Thus they can be used as a basis for performing genetic therapy. Alternatively, drug screening can be performed with originally normal cardiomyocytes that have been modified by recombinant DNA techniques to overexpress receptor protein or RNA and/or express variant receptor protein or RNA.

Drug screening assays can also be performed in transgenic animal models such as those described herein. Thus, naturally-occurring mutants or mutants made in a laboratory can be used to create transgenic animals that serve as a basis for drug screening. This model is particularly useful in assessing the total effect of an in vivo environment on the effect of a given drug. These animals can serve as an animal model for disease, such as cardiovascular diseases, so that in addition to ascertaining an effect on the specific mutant, an effect can be ascertained on the total system. Transgenic animals can thus be created that overexpress the receptor protein or express a variant, leading to, for example, cardiomyocyte hypertrophy. Alternatively, such animals can be created that underexpress the receptor or, in the case of "knockout" mice, lack one or more copies of the gene. Variant genes include all of the modifications described herein, such as insertion, deletion, and nucleotide substitutions. In one embodiment, gene expression is under the control of an inducible promoter. Therefore, modulation of the gene and, thus, modulation of the disease state is provided. The invention thus also encompasses cardiomyocytes derived from transgenic animals in which the cardiovascular disease has been produced by means of expression of the receptor in recombinant host cells, is naturally occurring, or occurs as the result of other protocols and/or agents.

The polypeptides can be used to identify compounds that modulate receptor activity. Both 14273 protein and appropriate variants and fragments can be used in high-throughput screens to assay candidate compounds for the ability to bind to the receptor. These compounds can be further screened against a functional receptor to determine the effect of the compound on the receptor activity. Compounds can be identified that activate (agonist) or inactivate (antagonist) the receptor to a desired degree.

The terms "agonist" and "antagonist" represent compounds that enhance or diminish a response. As one form of an agonist, the compound binds to the same site as the endogenous compound and produces the same type of signal, usually of equal or greater magnitude than the endogenous agent. Another form of agonist binds to a different site than the first agonist, producing no signal by itself; however, an enhanced signal is generated when the endogenous agent also binds to its site. This is called an allosteric action. One form of antagonist binds to the site used by the endogenous agent and diminishes or blocks the signal generated by the endogenous agent. Another form of antagonist binds to an allosteric site, similar to the second form of agonist, but produces a diminished signal generated by the endogenous agent. A third form of antagonist dissolves in the membrane or crosses the membrane and intercepts the signal generated by the endogenous agent within the membrane or on the intracellular side. An antagonist, accordingly, encompasses negative agonists or "inverse agonists", having a negative intrinsic activity that reduces the receptor signal activity relative to the signaling activity measured in the absence of the inverse agonist. Such an antagonist is distinguished from an antagonist having no intrinsic activity and no effect on the receptor's basal activity. Thus, for example, an inverse agonist could alter the receptor confirmation, thereby reducing or eliminating interaction with a ligand. See, Milligan et al., *TIPS* 16:10 (1995).

The receptor polypeptides can be used to screen a compound for the ability to stimulate or inhibit interaction between the receptor protein and a target molecule that normally interacts with the receptor protein. The target can be ligand or a component of the signal pathway with which the receptor protein normally interacts (for example, a G-protein or other interactor involved in cAMP or phosphatidylinositol turnover and/or adenylate cyclase, or phospholipase C activation). The assay includes the steps of combining the receptor protein with a candidate compound under conditions that allow the receptor protein or fragment to interact with the target molecule, and to detect the formation of a complex between the protein and the target or to detect the biochemical consequence of the interaction with the receptor protein and the target, such as any of the associated effects of signal transduction, such as ion flux, G-protein phosphorylation, cyclic AMP or phosphatidylinositol turnover, and adenylate cyclase or phospholipase C activation.

The receptor polypeptides are useful in cell based assays when they are overexpressed in a cell. Accordingly, such cells overexpressing the receptor are useful to identify compounds that are capable of modulating or compensating for the overexpression. Cells overexpressing the receptor can be derived from natural sources or can be created by routine recombinant methods.

The receptor polypeptides are also useful for screening compounds in a cell based assay when constitutively activated on a cell. Such cells expressing constitutively activated receptors are useful for screening compounds that modulate receptor activation. Such cells can be derived from natural sources or can be created by recombinant means that are well known in the art. For example, see Scheer et al., *J. Receptor Signal Transduction Res.* 17:57-73 (1997); U.S. Pat. No. 5,750,353.

Candidate compounds include, for example, 1) peptides such as soluble peptides, including Ig-tailed fusion peptides and members of random peptide libraries (see, e.g., Lam et al., *Nature* 354:82-84 (1991); Houghten et al., *Nature* 354: 84-86 (1991)) and combinatorial chemistry-derived molecular libraries made of D- and/or L-configuration amino acids; 2) phosphopeptides (e.g., members of random and partially degenerate, directed phosphopeptide libraries, see, e.g., Songyang et al., *Cell* 72:767-778 (1993)); 3) antibodies (e.g., polyclonal, monoclonal, humanized, anti-idiotypic, chimeric, and single chain antibodies as well as Fab, $F(ab')_2$, Fab expression library fragments, and epitope-binding fragments of antibodies); and 4) small organic and inorganic molecules (e.g., molecules obtained from combinatorial and natural product libraries).

One candidate compound is a soluble full-length receptor or fragment that competes for ligand binding. Other candidate compounds include mutant receptors or appropriate fragments containing mutations that affect receptor function and thus compete for ligand. Accordingly, a fragment that competes for ligand, for example with a higher affinity, or a fragment that binds ligand but does not allow release, is encompassed by the invention.

The invention provides other end points to identify compounds that modulate (stimulate or inhibit) receptor activity. The assays typically involve an assay of events in the signal transduction pathway that indicate receptor activity. Thus, the expression of genes that are up- or down-regulated in response to the receptor protein dependent signal cascade can be assayed. In one embodiment, the regulatory region of such genes can be operably linked to a marker that is easily detectable, such as luciferase. Alternatively, phosphorylation of the receptor protein, or a receptor protein target, could also be measured.

It is also understood that a disorder caused by aberrant levels or mutations in the protein can be used as a basis for an endpoint. Accordingly, specific deviations in the development or course of the disorder in response to a compound that acts on the receptor can serve as an endpoint.

Any of the biological or biochemical functions mediated by the receptor can be used as an endpoint assay. These include all of the biochemical or biochemical/biological events described herein, in the references cited herein, incorporated by reference for these endpoint assay targets, and other functions known to those of ordinary skill in the art. These endpoints include, but are not limited to, cardiomyocyte enlargement, gross enlargement of the heart, including enlargement of the atrium, atrial thrombi, chest edema, biventricular dilatation, and interstitial fibrosis.

Binding and/or activating compounds can also be screened by using chimeric receptor proteins in which the amino terminal extracellular domain, or parts thereof, the entire transmembrane domain or subregions, such as any of the seven transmembrane segments or any of the intracellular or extracellular loops and the carboxy terminal intracellular domain, or parts thereof, can be replaced by heterologous domains or subregions. For example, a G-protein-binding region can be used that interacts with a different G-protein then that which is recognized by the native receptor. Accordingly, a different set of signal transduction components is available as an endpoint assay for activation. Alternatively, the entire transmembrane portion or subregions (such as transmembrane segments or intracellular or extracellular loops) can be replaced with the entire transmembrane portion or subregions specific to a host cell that is different from the host cell from which the amino terminal extracellular domain and/or the G-protein-binding region are derived. This allows for assays to be performed in other than the specific host cell from which the receptor is derived. Alternatively, the amino terminal extracellular domain (and/or other ligand-binding regions) could be replaced by a domain (and/or other binding region) binding a different ligand, thus, providing an assay for test compounds that interact with the heterologous amino terminal extracellular domain (or region) but still cause signal transduction. Finally, activation can be detected by a reporter gene containing an easily detectable coding region operably linked to a transcriptional regulatory sequence that is part of the native signal transduction pathway.

The receptor polypeptides are also useful in competition binding assays in methods designed to discover compounds that interact with the receptor. Thus, a compound is exposed to a receptor polypeptide under conditions that allow the compound to bind or to otherwise interact with the polypeptide. Soluble receptor polypeptide is also added to the mixture. If the test compound interacts with the soluble receptor polypeptide, it decreases the amount of complex formed or activity from the receptor target. This type of assay is particularly useful in cases in which compounds are sought that interact with specific regions of the receptor. Thus, the soluble polypeptide that competes with the target receptor region is designed to contain peptide sequences corresponding to the region of interest.

To perform cell-free drug screening assays, it is desirable to immobilize either the receptor protein, or fragment, or its target molecule to facilitate separation of complexes from uncomplexed forms of one or both of the proteins, as well as to accommodate automation of the assay.

Techniques for immobilizing proteins on matrices can be used in the drug screening assays. In one embodiment, a fusion protein can be provided which adds a domain that allows the protein to be bound to a matrix. For example, glutathione-S-transferase/14273 fusion proteins can be adsorbed onto glutathione sepharose beads (Sigma Chemical, St. Louis, Mo.) or glutathione derivatized microtitre plates, which are then combined with the cell lysates (e.g., $^{35}$S-labeled) and the candidate compound, and the mixture incubated under conditions conducive to complex formation (e.g., at physiological conditions for salt and pH). Following incubation, the beads are washed to remove any unbound label, and the matrix immobilized and radiolabel determined directly, or in the supernatant after the complexes are dissociated. Alternatively, the complexes can be dissociated from the matrix, separated by SDS-PAGE, and the level of receptor-binding protein found in the bead fraction quantitated from the gel using standard electrophoretic techniques. For example, either the polypeptide or its target molecule can be immobilized utilizing conjugation of biotin and streptavidin using techniques well known in the art. Alternatively, antibodies reactive with the protein but which do not interfere with binding of the protein to its target molecule can be derivatized to the wells of the plate, and the protein trapped in the wells by antibody conjugation. Preparations of a receptor-binding protein and a candidate compound are incubated in the receptor protein-presenting wells and the amount of complex trapped in the well can be quantitated. Methods for detecting such complexes, in addition to those described above for the GST-immobilized complexes, include immunodetection of complexes using antibodies reactive with the receptor protein target molecule, or which are reactive with receptor protein and compete with the target molecule; as well as enzyme-linked assays which rely on detecting an enzymatic activity associated with the target molecule.

Modulators of receptor protein activity identified according to these drug screening assays can be used to treat a subject with a disorder mediated by the receptor pathway, by treating cells that express the 14273 protein, such as in heart, skeletal muscle, thymus, prostate, and uterus. These methods of treatment include the steps of administering the modulators of protein activity in a pharmaceutical composition as described herein, to a subject in need of such treatment. Preferred cells include, but are not limited to, cardiomyocytes, and particularly enlarged cardiomyocytes.

The receptor polypeptides also are useful to provide a target for diagnosing a disease or predisposition to disease mediated by the receptor protein, especially in heart, skeletal muscle, thymus, uterus, and prostate. The heart is an especially preferred target, and particularly cardiac myocytes, which have been shown by the inventors as subject to hypertrophy as a result of overexpression of the receptor protein. Accordingly, methods are provided for detecting the presence, or levels of, the receptor protein in a cell, tissue, or organism. The method involves contacting a biological sample with a compound capable of interacting with the receptor protein such that the interaction can be detected.

One agent for detecting receptor protein is an antibody capable of selectively binding to receptor protein. A biological sample includes tissues, cells and biological fluids isolated from a subject, as well as tissues, cells and fluids present within a subject.

The receptor protein also provides a target for diagnosing active disease, or predisposition to disease, in a patient having a variant receptor protein. Thus, receptor protein can be isolated from a biological sample, assayed for the presence of a genetic mutation that results in aberrant receptor protein. This includes amino acid substitution, deletion, insertion, rearrangement, (as the result of aberrant splicing events), and inappropriate post-translational modification. Analytic methods include altered electrophoretic mobility, altered tryptic peptide digest, altered receptor activity in cell-based or cell-free assay, alteration in ligand or antibody-binding pattern, altered isoelectric point, direct amino acid sequencing, and any other of the known assay techniques useful for detecting mutations in a protein.

In vitro techniques for detection of receptor protein include enzyme linked immunosorbent assays (ELISAs), Western blots, immunoprecipitations and immunofluorescence. Alternatively, the protein can be detected in vivo in a subject by introducing into the subject a labeled anti-receptor antibody. For example, the antibody can be labeled with a radioactive marker whose presence and location in a subject can be detected by standard imaging techniques. Particularly useful are methods which detect the alletic variant of a receptor protein expressed in a subject and methods which detect fragments of a receptor protein in a sample.

The receptor polypeptides are also useful in pharmacogenomic analysis. Pharmacogenomics deal with clinically significant hereditary variations in the response to drugs due to altered drug disposition and abnormal action in affected persons. See, e.g., Eichelbaum, M., *Clin. Exp. Pharmacol. Physiol.* 23(10-11):983-985 (1996), and Linder, M. W., *Clin. Chem.* 43(2):254-266 (1997). The clinical outcomes of these variations result in severe toxicity of therapeutic drugs in certain individuals or therapeutic failure of drugs in certain individuals as a result of individual variation in metabolism. Thus, the genotype of the individual can determine the way a therapeutic compound acts on the body or the way the body metabolizes the compound. Further, the activity of drug metabolizing enzymes effects both the intensity and duration of drug action. Thus, the pharmacogenomics of the individual permit the selection of effective compounds and effective dosages of such compounds for prophylactic or therapeutic treatment based on the individual's genotype. The discovery of genetic polymorphisms in some drug metabolizing enzymes has explained why some patients do not obtain the expected drug effects, show an exaggerated drug effect, or experience serious toxicity from standard drug dosages. Polymorphisms can be expressed in the phenotype of the extensive metabolizer and the phenotype of the poor metabolizer. Accordingly, genetic polymorphism may lead to allelic protein variants of the receptor protein in which one or more of the receptor functions in one population is different from those in another population. The polypeptides thus allow a target to ascertain a genetic predisposition that can affect treatment modality. Thus, in a ligand-based treatment, polymorphism may give rise to amino terminal extracellular domains and/or other ligand-binding regions that are more or less active in ligand binding, and receptor activation. Accordingly, ligand dosage would necessarily be modified to maximize the therapeutic effect within a given population containing a polymorphism. As an alternative to genotyping, specific polymorphic polypeptides could be identified.

The receptor polypeptides are also useful for monitoring therapeutic effects during clinical trials and other treatment. Thus, the therapeutic effectiveness of an agent that is designed to increase or decrease gene expression, protein levels or receptor activity can be monitored over the course of treatment using the receptor polypeptides as an end-point target.

The receptor polypeptides are also useful for treating a receptor-associated disorder. Accordingly, methods for treatment include the use of soluble receptor or fragments of the receptor protein that compete for ligand binding. These receptors or fragments can have a higher affinity for the ligand so as to provide effective competition.

Antibodies

The invention also provides antibodies that selectively bind to the 14273 receptor protein and its variants and fragments. An antibody is considered to selectively bind, even if it also binds to other proteins that are not substantially homologous with the receptor protein. These other proteins share homology with a fragment or domain of the receptor protein. This conservation in specific regions gives rise to antibodies that bind to both proteins by virtue of the homologous sequence. In this case, it would be understood that antibody binding to the receptor protein is still selective. Preferred antibodies bind to receptor mutants that are correlated with hypertrophy in myocytes, and correlated with cardiovascular disease.

To generate antibodies, an isolated receptor polypeptide is used as an immunogen to generate antibodies using standard techniques for polyclonal and monoclonal antibody preparation. Either the full-length protein or antigenic peptide fragment can be used. Regions having a high antigenicity index are shown in FIGS. 3 and 9.

Antibodies are preferably prepared from these regions or from discrete fragments in these regions. However, antibodies can be prepared from any region of the peptide as described herein. A preferred fragment produces an antibody that diminishes or completely prevents ligand-binding. Antibodies can be developed against the entire receptor or portions of the receptor, for example, the intracellular carboxy terminal domain, the amino terminal extracellular domain, the entire transmembrane domain or specific segments, any of the intra or extracellular loops, or any portions of the above. Antibodies may also be developed against specific functional sites, such as the site of ligand-binding, the site of G protein coupling, or sites that are glycosylated, phosphorylated, myristoylated, or amidated.

An antigenic fragment will typically comprise at least 6 contiguous amino acid residues. The antigenic peptide can comprise, however, at least 12, at least 14 amino acid residues, at least 15 amino acid residues, at least 20 amino acid residues, or at least 30 amino acid residues. In one embodiment, fragments correspond to regions that are located on the surface of the protein, e.g., hydrophilic regions. These fragments are not to be construed, however, as encompassing any fragments which may be disclosed prior to the invention.

Antibodies can be polyclonal or monoclonal. An intact antibody, or a fragment thereof (e.g. Fab or F(ab')$_2$) can be used.

Detection can be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}$I, $^{131}$I, $^{35}$S or $^{3}$H.

An appropriate immunogenic preparation can be derived from native, recombinantly expressed, protein or chemically synthesized peptides.

Antibody Uses

Since expression of the 14273 receptor has been correlated with cardiovascular disease, the uses of antibodies described below preferably apply to antibodies made from modified receptor proteins derived from cells affected by the disease, which can be used specifically to treat or diagnose the disease. It is also understood, however, that antibodies can also be used to treat the disease where the receptor is overexpressed, by binding to and inactivating overexpressed copies of the receptor protein. This can be done by introducing the antibodies extracellularly or by means of "intrabodies". Preferred cells include, but are not limited to, myocytes, especially hypertrophic cardiac myocytes. Thus, in preferred embodiments, the antibody uses described below preferably apply to tissues involved in heart disease.

The antibodies can be used to isolate a receptor protein by standard techniques, such as affinity chromatography or immunoprecipitation. In one embodiment, an antibody is prepared against a C-terminal antigenic sequence (SEQ ID NO:12, corresponds to amino acids 348-361 of SEQ ID NO:1), DTSVKRNDLSIISG. Accordingly, an antibody can be derived from these particular amino acids or from this approximate region. The antibodies can facilitate the purification of the natural receptor protein from cells and recombinantly produced receptor protein expressed in host cells.

The antibodies are useful to detect the presence of receptor protein in cells or tissues to determine the pattern of expression of the receptor among various tissues in an organism and over the course of normal development.

The antibodies can be used to detect receptor protein in situ, in vitro, or in a cell lysate or supernatant in order to evaluate the abundance and pattern of expression.

The antibodies can be used to assess abnormal tissue distribution or abnormal expression during development.

Antibody detection of circulating fragments of the full length receptor protein can be used to identify receptor turnover.

Further, the antibodies can be used to assess receptor expression in disease states, such as in active stages of the disease or in an individual with a predisposition toward disease related to receptor function, such as cardiovascular disease. When a disorder is caused by an inappropriate tissue distribution, developmental expression, or level of expression of the receptor protein, the antibody can be prepared against the normal receptor protein. If a disorder is characterized by a specific mutation in the receptor protein, antibodies specific for this mutant protein can be used to assay for the presence of the specific mutant receptor protein. However, intracellularly-made antibodies ("intrabodies") are also encompassed, which would recognize intracellular receptor peptide regions.

The antibodies can also be used to assess normal and aberrant subcellular localization of cells in the various tissues in an organism. Antibodies can be developed against the whole receptor or portions of the receptor, for example, portions of the amino terminal extracellular domain or extracellular loops.

The diagnostic uses can be applied, not only in genetic testing, but also in monitoring a treatment modality. Accordingly, where treatment is ultimately aimed at correcting receptor expression level or the presence of aberrant receptors and aberrant tissue distribution or developmental expression, antibodies directed against the receptor or relevant fragments can be used to monitor therapeutic efficacy.

Additionally, antibodies are useful in pharmacogenomic analysis. Thus, antibodies prepared against polymorphic receptor proteins can be used to identify individuals that require modified treatment modalities.

The antibodies are also useful as diagnostic tools as an immunological marker for aberrant receptor protein analyzed by electrophoretic mobility, isoelectric point, tryptic peptide digest, and other physical assays known to those in the art.

The antibodies are also useful for tissue typing. Thus, where a specific receptor protein has been correlated with expression in a specific tissue, antibodies that are specific for this receptor protein can be used to identify a tissue type.

The antibodies are also useful in forensic identification. Accordingly, where an individual has been correlated with a specific genetic polymorphism resulting in a specific polymorphic protein, an antibody specific for the polymorphic protein can be used as an aid in identification.

The antibodies are also useful for inhibiting receptor function, for example, blocking ligand binding.

These uses can also be applied in a therapeutic context in which treatment involves inhibiting receptor function. An antibody can be used, for example, to block ligand binding. Antibodies can be prepared against specific fragments containing sites required for function or against intact receptor associated with a cell.

The invention also encompasses kits for using antibodies to detect the presence of a receptor protein in a biological sample. The kit can comprise antibodies such as a labeled or labelable antibody and a compound or agent for detecting receptor protein in a biological sample; means for determining the amount of receptor protein in the sample; and means for comparing the amount of receptor protein in the sample with a standard. The compound or agent can be packaged in a suitable container. The kit can further comprise instructions for using the kit to detect receptor protein.

Polynucleotides

The nucleotide sequence in SEQ ID NO:2 and SEQ ID NO:5 was obtained by sequencing the deposited full length cDNA. Accordingly, the sequence of the deposited clone is controlling as to any discrepancies between the two and any reference to the sequence of SEQ ID NO:2 and SEQ ID NO:5 includes reference to the sequence of the deposited cDNA.

The specifically disclosed cDNA comprises the coding region and 5' and 3' untranslated sequences.

The human 14273 receptor cDNA is approximately 1743 nucleotides in length and encodes a full length protein that is approximately 361 amino acid residues in length. The nucleic acid is expressed in fetal brain, heart, skeletal muscle, thymus, prostate, placenta, and uterus. Structural analysis of the amino acid sequence of SEQ ID NO:1 and SEQ ID NO:4 is provided in FIGS. 3 and 9, a hydropathy plot. The figures show the putative structure of the seven transmembrane segments, the amino terminal extracellular domain and the carboxy terminal intracellular domain.

As used herein, the term "transmembrane segment" refers to a structural amino acid motif which includes a hydrophobic helix that spans the plasma membrane. The entire transmembrane domain spans from about amino acid 46 to about amino acid 321 of SEQ ID NO:1 or SEQ ID NO:4.

Seven segments span the membrane and there are three intracellular and three extracellular loops in this domain.

The invention provides isolated polynucleotides encoding a 14273 receptor protein. The term "14273 polynucleotide" or "14273 nucleic acid" refers to the sequence shown in SEQ ID NO:2 and SEQ ID NO:5 or in the deposited cDNA. The term "receptor polynucleotide" or "receptor nucleic acid" further includes variants and fragments of the 14273 polynucleotide.

An "isolated" receptor nucleic acid is one that is separated from other nucleic acid present in the natural source of the receptor nucleic acid. Preferably, an "isolated" nucleic acid is free of sequences which naturally flank the nucleic acid (i.e., sequences located at the 5' and 3' ends of the nucleic acid) in the genomic DNA of the organism from which the nucleic acid is derived. However, there can be some flanking nucleotide sequences, for example up to about 5 KB. The important point is that the nucleic acid is isolated from flanking sequences such that it can be subjected to the specific manipulations described herein such as recombinant expression, preparation of probes and primers, and other uses specific to the receptor nucleic acid sequences.

Moreover, an "isolated" nucleic acid molecule, such as a cDNA molecule, can be substantially free of other cellular material, or culture medium when produced by recombinant techniques, or chemical precursors or other chemicals when chemically synthesized. However, the nucleic acid molecule can be fused to other coding or regulatory sequences and still be considered isolated.

For example, recombinant DNA molecules contained in a vector are considered isolated. Further examples of isolated DNA molecules include recombinant DNA molecules maintained in heterologous host cells or purified (partially or substantially) DNA molecules in solution. Isolated RNA molecules include in vivo or in vitro RNA transcripts of the isolated DNA molecules of the present invention. Isolated nucleic acid molecules according to the present invention further include such molecules produced synthetically.

The receptor polynucleotides can encode the mature protein plus additional amino or carboxyl-terminal amino acids, or amino acids interior to the mature polypeptide (when the mature form has more than one polypeptide chain, for instance). Such sequences may play a role in processing of a protein from precursor to a mature form, facilitate protein trafficking, prolong or shorten protein half-life or facilitate manipulation of a protein for assay or production, among other things. As generally is the case in situ, the additional amino acids may be processed away from the mature protein by cellular enzymes.

The receptor polynucleotides include, but are not limited to, the sequence encoding the mature polypeptide alone, the sequence encoding the mature polypeptide and additional coding sequences, such as a leader or secretory sequence (e.g., a pre-pro or pro-protein sequence), the sequence encoding the mature polypeptide, with or without the additional coding sequences, plus additional non-coding sequences, for example introns and non-coding 5' and 3' sequences such as transcribed but non-translated sequences that play a role in transcription, mRNA processing (including splicing and polyadenylation signals), ribosome binding and stability of mRNA. In addition, the polynucleotide may be fused to a marker sequence encoding, for example, a peptide that facilitates purification.

Receptor polynucleotides can be in the form of RNA, such as mRNA, or in the form DNA, including cDNA and genomic DNA obtained by cloning or produced by chemical synthetic techniques or by a combination thereof. The nucleic acid, especially DNA, can be double-stranded or single-stranded. Single-stranded nucleic acid can be the coding strand (sense strand) or the non-coding strand (anti-sense strand).

One receptor nucleic acid comprises the nucleotide sequence shown in SEQ ID NO:2, corresponding to human brain cDNA or the murine ortholog shown in SEQ ID NO:5.

In one embodiment, the receptor nucleic acid comprises only the coding region.

The invention further provides variant receptor polynucleotides, and fragments thereof, that differ from the nucleotide sequence shown in SEQ ID NO:2 or SEQ ID NO:5 due to degeneracy of the genetic code and thus encode the same protein as that encoded by the nucleotide sequence shown in SEQ ID NO:2 or SEQ ID NO:5.

The invention also provides receptor nucleic acid molecules encoding the variant polypeptides described herein. Such polynucleotides may be naturally occurring, such as allelic variants (same locus), homologs (different locus), and orthologs (different organism), or may be constructed by recombinant DNA methods or by chemical synthesis. Such non-naturally occurring variants may be made by mutagenesis techniques, including those applied to polynucleotides, cells, or organisms. Accordingly, as discussed above, the variants can contain nucleotide substitutions, deletions, inversions and insertions.

Variation can occur in either or both the coding and non-coding regions. The variations can produce both conservative and non-conservative amino acid substitutions.

Orthologs, homologs, and allelic variants can be identified using methods well known in the art. These variants comprise a nucleotide sequence encoding a receptor that is 50%, at least about 55%, typically at least about 70-75%, more typically at least about 80-85%, and most typically at least about 90-95% or more homologous to the nucleotide sequence shown in SEQ ID NO:2 or SEQ ID NO:5 or a fragment of this sequence. Such nucleic acid molecules can readily be identified as being able to hybridize under stringent conditions, to the nucleotide sequence shown in SEQ ID NO:2 or SEQ ID NO:5 or a fragment of the sequence. It is understood that stringent hybridization does not indicate substantial homology where it is due to general homology, such as poly A sequences, or sequences common to all or most proteins, all GPCRs, or all family I GPCRs or sequences found dispersed throughout the genome that are not specific to any genes, for example, homopolymer stretches. Moreover, it is understood that variants do not include any of the nucleic acid sequences that may have been disclosed prior to the invention. Preferred variants include those that are correlated with hypertrophy of cardiac myocytes and with congestive heart failure.

As used herein, the term "hybridizes under stringent conditions" is intended to describe conditions for hybridization and washing under which nucleotide sequences encoding a receptor at least 50%, 55% homologous to each other typically remain hybridized to each other. The conditions can be such that sequences at least about 65%, at least about 70%, or at least about 75% or more homologous to each other typically remain hybridized to each other. Such stringent conditions are known to those skilled in the art and can be found in *Current Protocols in Molecular Biology*, John Wiley & Sons, N.Y. (1989), 6.3.1-6.3.6. One example of stringent hybridization conditions are hybridization in 6× sodium chloride/sodium citrate (SSC) at about 45° C., followed by one or more washes in 0.2×SSC, 0.1% SDS at 50-65° C. In one embodiment, an isolated receptor nucleic acid molecule that hybridizes under stringent conditions to the sequence of SEQ ID NO:2 corresponds to a naturally-occurring nucleic acid molecule. As used herein, a "naturally-occurring" nucleic acid molecule refers to an RNA or DNA molecule having a nucleotide sequence that occurs in nature (e.g., encodes a natural protein).

Furthermore, the invention provides polynucleotides that comprise a fragment of the full length receptor polynucleotides. The fragment can be single or double stranded and can comprise DNA or RNA. The fragment can be derived from either the coding or the non-coding sequence.

In one embodiment, an isolated receptor nucleic acid fragment is at least 5 nucleotides in length and is derived from the sequence from 1-410, 118-1295, or 1630-1743 nucleotides in length and hybridizes under stringent conditions to the nucleotide molecule comprising the nucleotide sequence of SEQ ID NO:2 or SEQ ID NO:5. In other embodiments, the nucleic acid is at least 10, 15, 20, 30, 40, 50, 100, 250, or 500 nucleotides in length or greater.

In another embodiment, the fragment comprises contiguous nucleotides from around 410 to around 442 of SEQ ID NO:2 or SEQ ID NO:5 that are greater than 13, 442-473 of SEQ ID NO:2 or SEQ ID NO:5 that are greater than 26, 605-745 of SEQ ID NO:2 or SEQ ID NO:5 that are greater than 44, 745-857 of SEQ ID NO:2 or SEQ ID NO:5 that are greater than 17, 857-924 of SEQ ID NO:2 or SEQ ID NO:5 that are greater than 23, 925-1118 of SEQ ID NO:2 or SEQ ID NO:5 that are greater than 23, and 1295-1630 of SEQ ID NO:2 or SEQ ID NO:5 that are greater than 25.

In another embodiment an isolated receptor nucleic acid encodes the entire coding region from amino acid 1 to amino acid 321 of SEQ ID NO:1 or SEQ ID NO:4. In another embodiment the isolated receptor nucleic acid encodes a sequence corresponding to the mature protein from about amino acid 36 to amino acid 321 of SEQ ID NO:1 or SEQ ID NO:4. Other fragments include nucleotide sequences that include part, or all, of the coding region and extend into either the 5' or 3' noncoding region, or both of these regions. Other fragments include nucleotide sequences encoding the amino acid fragments described herein. Further fragments can include subfragments of the specific domains or sites described herein. Fragments also include nucleic acid sequences corresponding to specific amino acid sequences described above or fragments thereof. Nucleic acid fragments, according to the present invention, are not to be construed as encompassing those fragments that may have been disclosed prior to the invention.

Receptor nucleic acid fragments further include sequences corresponding to the domains described herein, subregions also described, and specific functional sites. Receptor nucleic acid fragments also include combinations of the domains, segments, loops, and other functional sites described above. Thus, for example, a receptor nucleic acid could include sequences corresponding to the amino terminal extracellular domain and one transmembrane fragment. A person of ordinary skill in the art would be aware of the many permutations that are possible.

However, it is understood that a receptor fragment includes any nucleic acid sequence that does not include the entire gene.

Receptor nucleic acid fragments include nucleic acid molecules encoding a polypeptide comprising the amino terminal extracellular domain including amino acid residues from 1 to about 45 of SEQ ID NO:1 or SEQ ID NO:4, a polypeptide comprising the region spanning the transmembrane domain (amino acid residues from about 46 to about 321 of SEQ ID NO:1 or SEQ ID NO:4), a polypeptide comprising the carboxy terminal intracellular domain (amino acid residues from about 322 to about 361 of SEQ ID NO:1 or SEQ ID NO:4), and a polypeptide encoding the G-protein receptor signature (135-136 or surrounding amino acid residues from about 125 to about 145 of SEQ ID NO:1 or SEQ ID NO:4), nucleic acid molecules encoding any of the seven transmembrane segments, extracellular or intracellular loops, glycosylation, phosphorylation, myristoylation, and amidation sites. Where the location of the domains have been predicted by computer analysis, one of ordinary skill would appreciate that the amino acid residues constituting these domains can vary depending on the criteria used to define the domains.

The invention also provides receptor nucleic acid fragments that encode epitope bearing regions of the receptor proteins described herein.

The isolated receptor polynucleotide sequences, and especially fragments, are useful as DNA probes and primers.

For example, the coding region of a receptor gene can be isolated using the known nucleotide sequence to synthesize an oligonucleotide probe. A labeled probe can then be used to screen a cDNA library, genomic DNA library, or mRNA to isolate nucleic acid corresponding to the coding region. Further, primers can be used in PCR reactions to clone specific regions of receptor genes.

A probe/primer typically comprises substantially purified oligonucleotide. The oligonucleotide typically comprises a region of nucleotide sequence that hybridizes under stringent conditions to at least about 10, 12, typically about 25, more typically about 40, 50 or 75 consecutive nucleotides of SEQ ID NO:2 or SEQ ID NO:5 sense or anti-sense strand or other receptor polynucleotides. A probe further comprises a label, e.g., radioisotope, fluorescent compound, enzyme, or enzyme co-factor.

Polynucleotide Uses

Since zexpression of the 14273 receptor has been associated with cardiovascular disease, the polynucleotides described herein can be used for treatment and diagnosis of patients having, or predisposed to having, cardiovascular disease, including, but not limited to, congestive heart failure. The induction of receptor mRNA has been demonstrated by the inventors to occur in hypertrophic human cardiac myocytes, the induction being associated with morphological change. Accordingly, a preferred use of the polypeptides is for treatment and diagnosis of cardiovascular disease in which cardiomyocyte hypertrophy is involved. Such cardiovascular disease/disorders include, but are not limited to, dilation, ischemia, cardiac fibrosis, fibro-elastosis, general loss of cardiac muscle tone, and thrombosis.

The receptor polynucleotides are useful for probes, primers, and in biological assays. Where the polynucleotides are used to assess GPCR properties or functions, such as in the assays described herein, all or less than all of the entire cDNA can be useful. In this case, even fragments that may have been known prior to the invention are encompassed. Thus, for example, assays specifically directed to GPCR functions, such as assessing agonist or antagonist activity, encompass the use of known fragments. Further, diagnostic methods for assessing receptor function can also be practiced with any fragment, including those fragments that may have been known prior to the invention. Similarly, in methods involving treatment of receptor dysfunction, all fragments are encompassed, including those which may have been known in the art.

The receptor polynucleotides are useful as a hybridization probe for cDNA and genomic DNA to isolate a full-length cDNA and genomic clones encoding the polypeptide described in SEQ ID NO:1 or SEQ ID NO:4 and to isolate cDNA and genomic clones that correspond to variants producing the same polypeptide shown in SEQ ID NO:1 or SEQ ID NO:4 or the other variants described herein. Variants can be isolated from the same tissue and organism from which the polypeptide shown in SEQ ID NO:1 or SEQ ID NO:4 was isolated, different tissues from the same organism, or from different organisms. This method is useful for isolating genes and cDNA that are developmentally-controlled and therefore may be expressed in the same tissue or different tissues at different points in the development of an organism.

The probe can correspond to any sequence along the entire length of the gene encoding the receptor. Accordingly, it could be derived from 5' noncoding regions, the coding region, and 3' noncoding regions. It is understood, however, that the probe would not encompass a fragment already described prior to the invention.

The nucleic acid probe can be, for example, the full-length cDNA of SEQ ID NO:1 or SEQ ID NO:4, or a fragment thereof, such as an oligonucleotide of at least 10, 12, 15, 30, 50, 100, 250 or 500 nucleotides in length and sufficient to specifically hybridize under stringent conditions to mRNA or DNA.

Fragments of the polynucleotides described herein are also useful to synthesize larger fragments or full-length polynucleotides described herein. For example, a fragment can be hybridized to any portion of an mRNA and a larger or full-length cDNA can be produced.

The fragments are also useful to synthesize antisense molecules of desired length and sequence.

The receptor polynucleotides are also useful as primers for PCR to amplify any given region of a receptor polynucleotide.

The receptor polynucleotides are also useful for constructing recombinant vectors. Such vectors include expression vectors that express a portion of, or all of, the receptor polypeptides. Vectors also include insertion vectors, used to integrate into another polynucleotide sequence, such as into the cellular genome, to alter in situ expression of receptor genes and gene products. For example, an endogenous receptor coding sequence can be replaced via homologous recombination with all or part of the coding region containing one or more specifically introduced mutations.

The receptor polynucleotides are also useful for expressing antigenic portions of the receptor proteins.

The receptor polynucleotides are also useful as probes for determining the chromosomal positions of the receptor polynucleotides by means of in situ hybridization methods.

The receptor polynucleotide probes are also useful to determine patterns of the presence of the gene encoding the receptors and their variants with respect to tissue distribution, for example, whether gene duplication has occurred and whether the duplication occurs in all or only a subset of tissues. The genes can be naturally-occurring or can have been introduced into a cell, tissue, or organism exogenously.

The receptor polynucleotides are also useful for designing ribozymes corresponding to all, or a part, of the mRNA produced from genes encoding the polynucleotides described herein.

The receptor polynucleotides are also useful for constructing host cells expressing a part, or all, of the receptor polynucleotides and polypeptides.

The receptor polynucleotides are also useful for constructing transgenic animals expressing all, or a part, of the receptor polynucleotides and polypeptides. These animals are useful as model systems for GPCR-related disorders, such as congestive heart failure. Such animal models of cardiovascular diseases can then be used to test compounds for their effect, through the receptor gene or gene product, on the development or progression of the disease.

The receptor polynucleotides are also useful for making vectors that express part, or all, of the receptor polypeptides.

The receptor polynucleotides are also useful as hybridization probes for determining the level of receptor nucleic acid expression. Accordingly, the probes can be used to detect the presence of, or to determine levels of, receptor nucleic acid in cells, tissues, and in organisms. The nucleic acid whose level is determined can be DNA or RNA. Accordingly, probes corresponding to the polypeptides described herein can be used to assess gene copy number in a given cell, tissue, or organism. This is particularly relevant in cases in which there has been an amplification of the receptor genes.

Alternatively, the probe can be used in an in situ hybridization context to assess the position of extra copies of the receptor genes, as on extrachromosomal elements or as integrated into chromosomes in which the receptor gene is not normally found, for example as a homogeneously staining region.

These uses are relevant for diagnosis of disorders involving an increase or decrease in receptor expression relative to normal results.

In vitro techniques for detection of mRNA include Northern hybridizations and in situ hybridizations. In vitro techniques for detecting DNA includes Southern hybridizations and in situ hybridization.

Probes can be used as a part of a diagnostic test kit for identifying cells or tissues that express a receptor protein, such as by measuring a level of a receptor-encoding nucleic acid in a sample of cells from a subject e.g., mRNA or genomic DNA, or determining if a receptor gene has been mutated.

Nucleic acid expression assays are useful for drug screening to identify compounds that modulate receptor nucleic acid expression.

The invention thus provides a method for identifying a compound that can be used to treat a disorder associated with nucleic acid expression of the receptor gene. The method typically includes assaying the ability of the compound to modulate the expression of the receptor nucleic acid and thus identifying a compound that can be used to treat a disorder characterized by undesired receptor nucleic acid expression.

The assays can be performed in cell-based and cell-free systems. Cell-based assays include cells naturally expressing the receptor nucleic acid or recombinant cells genetically engineered to express specific nucleic acid sequences.

Alternatively, candidate compounds can be assayed in vivo in patients or in transgenic animals. Thus, variant receptor nucleic acid that results in an increase in the level or a change in the nucleotide sequence can be introduced into a transgenic animal to serve as the target for a candidate compound. The mutation may be naturally-occurring or may be created in the laboratory.

The assay for receptor nucleic acid expression can involve direct assay of nucleic acid levels, such as mRNA levels, or on collateral compounds involved in the signal pathway (such as cyclic AMP or phosphatidylinositol turnover). Further, the expression of genes that are up- or down-regulated in response to the receptor protein signal pathway can also be assayed. In this embodiment the regulatory regions of these genes can be operably linked to a reporter gene such as luciferase.

Thus, modulators of receptor gene expression can be identified in a method wherein a cell is contacted with a candidate compound and the expression of mRNA determined. The level of expression of receptor mRNA in the presence of the candidate compound is compared to the level of expression of receptor mRNA in the absence of the candidate compound. The candidate compound can then be identified as a modulator of nucleic acid expression based on this comparison and be used, for example to treat a disorder characterized by aberrant nucleic acid expression. When expression of mRNA is statistically significantly greater in the presence of the candidate compound than in its absence, the candidate compound is identified as a stimulator of nucleic acid expression. When nucleic acid expression is statistically significantly less in the presence of the candidate compound than in its absence, the candidate compound is identified as an inhibitor of nucleic acid expression.

Accordingly, the invention provides methods of treatment, with the nucleic acid as a target, using a compound identified through drug screening as a gene modulator to modulate receptor nucleic acid expression. Modulation includes both up-regulation (i.e. activation or agonization) or down-regulation (suppression or antagonization) or nucleic acid expression.

Alternatively, a modulator for receptor nucleic acid expression can be a small molecule or drug identified using the screening assays described herein as long as the drug or small molecule inhibits the receptor nucleic acid expression.

The receptor polynucleotides are also useful for monitoring the effectiveness of modulating compounds on the expression or activity of the receptor gene in clinical trials or in a treatment regimen. Thus, the gene expression pattern can serve as a barometer for the continuing effectiveness of treatment with the compound, particularly with compounds to which a patient can develop resistance. The gene expression pattern can also serve as a marker indicative of a physiological response of the affected cells to the compound. Accordingly, such monitoring would allow either increased administration of the compound or the administration of alternative compounds to which the patient has not become resistant. Similarly, if the level of nucleic acid expression falls below a desirable level, administration of the compound could be commensurately decreased.

The receptor polynucleotides are also useful in diagnostic assays for qualitative changes in receptor nucleic acid, and particularly in qualitative changes that lead to pathology. The polynucleotides can be used to detect mutations in receptor genes and gene expression products such as mRNA. The polynucleotides can be used as hybridization probes to detect naturally-occurring genetic mutations in the receptor gene and thereby to determine whether a subject with the mutation is at risk for a disorder caused by the mutation. Mutations include deletion, addition, or substitution of one or more nucleotides in the gene, chromosomal rearrangement, such as inversion or transposition, modification of genomic DNA, such as aberrant methylation patterns or changes in gene copy number, such as amplification. Detection of a mutated form of the receptor gene associated with a dysfunction provides a diagnostic tool for an active disease or susceptibility to disease when the disease results from overexpression, underexpression, or altered expression of a receptor protein.

Individuals carrying mutations in the receptor gene can be detected at the nucleic acid level by a variety of techniques. Genomic DNA can be analyzed directly or can be amplified by using PCR prior to analysis. RNA or cDNA can be used in the same way.

In certain embodiments, detection of the mutation involves the use of a probe/primer in a polymerase chain reaction (PCR) (see, e.g. U.S. Pat. Nos. 4,683,195 and 4,683,202), such as anchor PCR or RACE PCR, or, alternatively, in a ligation chain reaction (LCR) (see, e.g., Landegran et al., Science 241:1077-1080 (1988); and Nakazawa et al., PNAS 91:360-364 (1994)), the latter of which can be particularly useful for detecting point mutations in the gene (see Abravaya et al., Nucleic Acids Res. 23:675-682 (1995)). This method can include the steps of collecting a sample of cells from a patient, isolating nucleic acid (e.g., genomic, mRNA or both) from the cells of the sample, contacting the nucleic acid sample with one or more primers which specifically hybridize to a gene under conditions such that hybridization and amplification of the gene (if present) occurs, and detecting the presence or absence of an amplification product, or detecting the size of the amplification product and comparing the length to a control sample. Deletions and insertions can be detected by a change in size of the amplified product compared to the normal genotype. Point mutations can be identified by hybridizing amplified DNA to normal RNA or antisense DNA sequences.

Alternatively, mutations in a receptor gene can be directly identified, for example, by alterations in restriction enzyme digestion patterns determined by gel electrophoresis.

Further, sequence-specific ribozymes (U.S. Pat. No. 5,498, 531) can be used to score for the presence of specific mutations by development or loss of a ribozyme cleavage site.

Perfectly matched sequences can be distinguished from mismatched sequences by nuclease cleavage digestion assays or by differences in melting temperature.

Sequence changes at specific locations can also be assessed by nuclease protection assays such as RNase and S1 protection or the chemical cleavage method.

Furthermore, sequence differences between a mutant receptor gene and a wild-type gene can be determined by direct DNA sequencing. A variety of automated sequencing procedures can be utilized when performing the diagnostic assays ((1995) Biotechniques 19:448), including sequencing by mass spectrometry (see, e.g., PCT International Publication No. WO 94/16101; Cohen et al., Adv. Chromatogr. 36:127-162 (1996); and Griffin et al., Appl. Biochem. Biotechnol. 38:147-159 (1993)).

Other methods for detecting mutations in the gene include methods in which protection from cleavage agents is used to detect mismatched bases in RNA/RNA or RNA/DNA duplexes (Myers et al., Science 230:1242 (1985)); Cotton et al., PNAS 85:4397 (1988); Saleeba et al., Meth. Enzymol. 217:286-295 (1992)), electrophoretic mobility of mutant and wild type nucleic acid is compared (Orita et al., PNAS 86:2766 (1989); Cotton et al., Mutat. Res. 285:125-144 (1993); and Hayashi et al., Genet. Anal. Tech. Appl. 9:73-79 (1992)), and movement of mutant or wild-type fragments in polyacrylamide gels containing a gradient of denaturant is assayed using denaturing gradient gel electrophoresis (Myers et al., Nature 313:495 (1985)). Examples of other techniques for detecting point mutations include selective oligonucleotide hybridization, selective amplification, and selective primer extension.

The receptor polynucleotides are also useful for testing an individual for a genotype that while not necessarily causing the disease, nevertheless affects the treatment modality. Thus, the polynucleotides can be used to study the relationship between an individual's genotype and the individual's response to a compound used for treatment (pharmacogenomic relationship). In the present case, for example, a mutation in the receptor gene that results in altered affinity for ligand could result in an excessive or decreased drug effect with standard concentrations of ligand that activates the receptor. Accordingly, the receptor polynucleotides described herein can be used to assess the mutation content of the receptor gene in an individual in order to select an appropriate compound or dosage regimen for treatment.

Thus polynucleotides displaying genetic variations that affect treatment provide a diagnostic target that can be used to tailor treatment in an individual. Accordingly, the production of recombinant cells and animals containing these polymorphisms allow effective clinical design of treatment compounds and dosage regimens.

The receptor polynucleotides are also useful for chromosome identification when the sequence is identified with an individual chromosome and to a particular location on the chromosome. First, the DNA sequence is matched to the chromosome by in situ or other chromosome-specific hybridization. Sequences can also be correlated to specific chromosomes by preparing PCR primers that can be used for PCR screening of somatic cell hybrids containing individual chromosomes from the desired species. Only hybrids containing the chromosome containing the gene homologous to the primer will yield an amplified fragment. Sublocalization can be achieved using chromosomal fragments. Other strategies include prescreening with labeled flow-sorted chromosomes and preselection by hybridization to chromosome-specific libraries. Further mapping strategies include fluorescence in situ hybridization which allows hybridization with probes shorter than those traditionally used. Reagents for chromosome mapping can be used individually to mark a single chromosome or a single site on the chromosome, or panels of reagents can be used for marking multiple sites and/or multiple chromosomes. Reagents corresponding to noncoding regions of the genes actually are preferred for mapping purposes. Coding sequences are more likely to be conserved within gene families, thus increasing the chance of cross hybridizations during chromosomal mapping.

The receptor polynucleotides can also be used to identify individuals from small biological samples. This can be done for example using restriction fragment-length polymorphism (RFLP) to identify an individual. Thus, the polynucleotides described herein are useful as DNA markers for RFLP (See U.S. Pat. No. 5,272,057).

Furthermore, the receptor sequence can be used to provide an alternative technique which determines the actual DNA sequence of selected fragments in the genome of an individual. Thus, the receptor sequences described herein can be used to prepare two PCR primers from the 5' and 3' ends of the sequences. These primers can then be used to amplify DNA from an individual for subsequent sequencing.

Panels of corresponding DNA sequences from individuals prepared in this manner can provide unique individual identifications, as each individual will have a unique set of such DNA sequences. It is estimated that allelic variation in humans occurs with a frequency of about once per each 500 bases. Allelic variation occurs to some degree in the coding regions of these sequences, and to a greater degree in the noncoding regions. The receptor sequences can be used to obtain such identification sequences from individuals and from tissue. The sequences represent unique fragments of the human genome. Each of the sequences described herein can, to some degree, be used as a standard against which DNA from an individual can be compared for identification purposes.

If a panel of reagents from the sequences is used to generate a unique identification database for an individual, those same reagents can later be used to identify tissue from that individual. Using the unique identification database, positive identification of the individual, living or dead, can be made from extremely small tissue samples.

The receptor polynucleotides can also be used in forensic identification procedures. PCR technology can be used to amplify DNA sequences taken from very small biological samples, such as a single hair follicle, body fluids (e.g. blood, saliva, or semen). The amplified sequence can then be compared to a standard allowing identification of the origin of the sample.

The receptor polynucleotides can thus be used to provide polynucleotide reagents, e.g., PCR primers, targeted to specific loci in the human genome, which can enhance the reliability of DNA-based forensic identifications by, for example, providing another "identification marker" (i.e. another DNA sequence that is unique to a particular individual). As described above, actual base sequence information can be used for identification as an accurate alternative to patterns formed by restriction enzyme generated fragments. Sequences targeted to the noncoding region are particularly useful since greater polymorphism occurs in the noncoding regions, making it easier to differentiate individuals using this technique. Fragments are at least 10 bases.

The receptor polynucleotides can further be used to provide polynucleotide reagents, e.g., labeled or labelable probes which can be used in, for example, an in situ hybridization technique, to identify a specific tissue. This is useful in cases in which a forensic pathologist is presented with a tissue of unknown origin. Panels of receptor probes can be used to identify tissue by species and/or by organ type.

In a similar fashion, these primers and probes can be used to screen tissue culture for contamination (i.e. screen for the presence of a mixture of different types of cells in a culture).

Alternatively, the receptor polynucleotides can be used directly to block transcription or translation of receptor gene sequences by means of antisense or ribozyme constructs. Thus, in a disorder characterized by abnormally high or undesirable receptor gene expression, as is the case for cardiovascular disease associated with cardiomyocyte hypertrophy, nucleic acids can be directly used for treatment.

The receptor polynucleotides are thus useful as antisense constructs to control receptor gene expression in cells, tissues, and organisms. A DNA antisense polynucleotide is designed to be complementary to a region of the gene involved in transcription, preventing transcription and hence production of receptor protein. An antisense RNA or DNA polynucleotide would hybridize to the mRNA and thus block translation of mRNA into receptor protein.

Examples of antisense molecules useful to inhibit nucleic acid expression include antisense molecules complementary to a fragment of the 5' untranslated region of SEQ ID NO:2 or SEQ ID NO:5 which also includes the start codon and antisense molecules which are complementary to a fragment of the 3' untranslated region of SEQ ID NO:2 or SEQ ID NO:5.

Alternatively, a class of antisense molecules can be used to inactivate mRNA in order to decrease expression of receptor nucleic acid. Accordingly, these molecules can treat a disorder characterized by abnormal or undesired receptor nucleic acid expression. This technique involves cleavage by means of ribozymes containing nucleotide sequences complementary to one or more regions in the mRNA that attenuate the ability of the mRNA to be translated. Possible regions include coding regions and particularly coding regions corresponding to the catalytic and other functional activities of the receptor protein, such as ligand binding.

The receptor polynucleotides also provide vectors for gene therapy in patients containing cells that are aberrant in receptor gene expression. Thus, recombinant cells, which include the patient's cells that have been engineered ex vivo and returned to the patient, are introduced into an individual where the cells produce the desired receptor protein to treat the individual.

The invention also encompasses kits for detecting the presence of a receptor nucleic acid in a biological sample. For example, the kit can comprise reagents such as a labeled or labelable nucleic acid or agent capable of detecting receptor nucleic acid in a biological sample; means for determining the amount of receptor nucleic acid in the sample; and means for comparing the amount of receptor nucleic acid in the sample with a standard. The compound or agent can be packaged in a suitable container. The kit can further comprise instructions for using the kit to detect receptor mRNA or DNA.

Vectors/Host Cells

The invention also provides vectors containing the receptor polynucleotides. The term "vector" refers to a vehicle, preferably a nucleic acid molecule, that can transport the receptor polynucleotides. When the vector is a nucleic acid molecule, the receptor polynucleotides are covalently linked to the vector nucleic acid. With this aspect of the invention, the vector includes a plasmid, single or double stranded phage, a single or double stranded RNA or DNA viral vector, or artificial chromosome, such as a BAC, PAC, YAC, OR MAC.

A vector can be maintained in the host cell as an extrachromosomal element where it replicates and produces additional copies of the receptor polynucleotides. Alternatively, the vector may integrate into the host cell genome and produce additional copies of the receptor polynucleotides when the host cell replicates.

The invention provides vectors for the maintenance (cloning vectors) or vectors for expression (expression vectors) of the receptor polynucleotides. The vectors can function in prokaryotic or eukaryotic cells or in both (shuttle vectors).

Expression vectors contain cis-acting regulatory regions that are operably linked in the vector to the receptor polynucleotides such that transcription of the polynucleotides is allowed in a host cell. The polynucleotides can be introduced into the host cell with a separate polynucleotide capable of affecting transcription. Thus, the second polynucleotide may provide a trans-acting factor interacting with the cis-regulatory control region to allow transcription of the receptor polynucleotides from the vector. Alternatively, a trans-acting factor may be supplied by the host cell. Finally, a trans-acting factor can be produced from the vector itself.

It is understood, however, that in some embodiments, transcription and/or translation of the receptor polynucleotides can occur in a cell-free system.

The regulatory sequence to which the polynucleotides described herein can be operably linked include promoters for directing mRNA transcription. These include, but are not limited to, the left promoter from bacteriophage λ, the lac, TRP, and TAC promoters from *E. coli*, the early and late promoters from SV40, the CMV immediate early promoter, the adenovirus early and late promoters, and retrovirus long-terminal repeats.

In addition to control regions that promote transcription, expression vectors may also include regions that modulate transcription, such as repressor binding sites and enhancers. Examples include the SV40 enhancer, the cytomegalovirus immediate early enhancer, polyoma enhancer, adenovirus enhancers, and retrovirus LTR enhancers.

In addition to containing sites for transcription initiation and control, expression vectors can also contain sequences necessary for transcription termination and, in the transcribed region a ribosome binding site for translation. Other regulatory control elements for expression include initiation and termination codons as well as polyadenylation signals. The person of ordinary skill in the art would be aware of the numerous regulatory sequences that are useful in expression vectors. Such regulatory sequences are described, for example, in Sambrook et al., *Molecular Cloning: A Laboratory Manual.* $2^{nd}$. *ed.*, Cold Spring Harbor Laboratory Press, Cold Spring Harbor, N.Y., (1989).

A variety of expression vectors can be used to express a receptor polynucleotide. Such vectors include chromosomal, episomal, and virus-derived vectors, for example vectors derived from bacterial plasmids, from bacteriophage, from yeast episomes, from yeast chromosomal elements, including yeast artificial chromosomes, from viruses such as baculoviruses, papovaviruses such as SV40, Vaccinia viruses, adenoviruses, poxviruses, pseudorabies viruses, and retroviruses. Vectors may also be derived from combinations of these sources such as those derived from plasmid and bacteriophage genetic elements, e.g. cosmids and phagemids. Appropriate cloning and expression vectors for prokaryotic and eukaryotic hosts are described in Sambrook et al., *Molecular Cloning: A Laboratory Manual.* $2^{nd}$. *ed.*, Cold Spring Harbor Laboratory Press, Cold Spring Harbor, N.Y., (1989).

The regulatory sequence may provide constitutive expression in one or more host cells (i.e. tissue specific) or may provide for inducible expression in one or more cell types such as by temperature, nutrient additive, or exogenous factor such as a hormone or other ligand. A variety of vectors providing for constitutive and inducible expression in prokaryotic and eukaryotic hosts are well known to those of ordinary skill in the art.

In one specifically disclosed embodiment, expression of the receptor gene is under control of the alpha-MHC promoter, that allows specific expression in cardiomyocytes. This promoter could be further modified so that it is specifically inducible in cardiomyocytes while also being specifically expressed in these cells.

The receptor polynucleotides can be inserted into the vector nucleic acid by well-known methodology. Generally, the DNA sequence that will ultimately be expressed is joined to an expression vector by cleaving the DNA sequence and the expression vector with one or more restriction enzymes and then ligating the fragments together. Procedures for restriction enzyme digestion and ligation are well known to those of ordinary skill in the art.

The vector containing the appropriate polynucleotide can be introduced into an appropriate host cell for propagation or expression using well-known techniques. Bacterial cells include, but are not limited to, *E. coli, Streptomyces*, and *Salmonella typhimurium*. Eukaryotic cells include, but are not limited to, yeast, insect cells such as *Drosophila*, animal cells such as COS, HEK 293, and CHO cells, and plant cells. It is understood that any of the established cell lines or any cell capable of being established are useful for producing long-term recombinant expression of the receptor polynucleotides. However, in some embodiments, it is useful to obtain recombinant expression in non-established cells as well.

As described herein, it may be desirable to express the polypeptide as a fusion protein. Accordingly, the invention provides fusion vectors that allow for the production of the receptor polypeptides. Fusion vectors can increase the expression of a recombinant protein, increase the solubility of the recombinant protein, and aid in the purification of the protein by acting for example as a ligand for affinity purification. A proteolytic cleavage site may be introduced at the junction of the fusion moiety so that the desired polypeptide can ultimately be separated from the fusion moiety. Proteolytic enzymes include, but are not limited to, factor Xa, thrombin, and enterokinase. Typical fusion expression vectors include pGEX (Smith et al., *Gene* 67:3140 (1988)), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein. Examples of suitable inducible non-fusion *E. coli* expression vectors include pTrc (Amann et al., *Gene* 69:301-315 (1988)) and pET 11d (Studier et al., *Gene Expression Technology: Methods in Enzymology* 185:60-89 (1990)).

Recombinant protein expression can be maximized in a host bacteria by providing a genetic background wherein the host cell has an impaired capacity to proteolytically cleave the recombinant protein. (Gottesman, S., *Gene Expression Technology: Methods in Enzymology* 185, Academic Press, San Diego, Calif. (1990) 119-128). Alternatively, the sequence of the polynucleotide of interest can be altered to provide preferential codon usage for a specific host cell, for example *E. coli*. (Wada et al., *Nucleic Acids Res.* 20:2111-2118 (1992)).

The receptor polynucleotides can also be expressed by expression vectors that are operative in yeast. Examples of vectors for expression in yeast e.g., *S. cerevisiae* include pYepSec1 (Baldari, et al., *EMBO J.* 6:229-234 (1987)), pMFa (Kurjan et al., *Cell* 30:933-943(1982)), pJRY88 (Schultz et al., *Gene* 54:113-123 (1987)), and pYES2 (Invitrogen Corporation, San Diego, Calif.).

The receptor polynucleotides can also be expressed in insect cells using, for example, baculovirus expression vectors. Baculovirus vectors available for expression of proteins in cultured insect cells (e.g., Sf 9 cells) include the pAc series (Smith et al., *Mol. Cell Biol.* 3:2156-2165 (1983)) and the pVL series (Lucklow et al., *Virology* 170:31-39 (1989)).

In certain embodiments of the invention, the polynucleotides described herein are expressed in mammalian cells using mammalian expression vectors. Examples of mammalian expression vectors include pCDM8 (Seed, B. *Nature* 329:840(1987)) and pMT2PC (Kaufman et al., *EMBO J.* 6:187-195 (1987)).

The expression vectors listed herein are provided by way of example only of the well-known vectors available to those of ordinary skill in the art that would be useful to express the receptor polynucleotides. The person of ordinary skill in the art would be aware of other vectors suitable for maintenance propagation or expression of the polynucleotides described herein. These are found for example in Sambrook, J., Fritsh, E. F., and Maniatis, T. *Molecular Cloning: A Laboratory Manual.* $2^{nd}$, *ed., Cold Spring Harbor Laboratory,* Cold Spring Harbor Laboratory Press, Cold Spring Harbor, N.Y., 1989.

The invention also encompasses vectors in which nucleic acid sequences described herein are cloned into the vector in reverse orientation, but operably linked to a regulatory sequence that permits transcription of antisense RNA.

Thus, an antisense transcript can be produced to all, or to a portion, of the polynucleotide sequences described herein, including both coding and non-coding regions. Expression of this antisense RNA is subject to each of the parameters described above in relation to expression of the sense RNA (regulatory sequences, constitutive or inducible expression, tissue-specific expression).

The invention also relates to recombinant host cells containing the vectors described herein. Host cells therefore include prokaryotic cells, lower eukaryotic cells such as yeast, other eukaryotic cells such as insect cells, and higher eukaryotic cells such as mammalian cells.

In a preferred embodiment, recombinant cells are cardiac myocytes. These can be derived from humans or other animals having or predisposed to having a cardiovascular disease involving hypertrophy of cardiomyocytes. The cardiomyocytes thus can be phenotypically normal or pathological, including at various stages of hypertrophy. Such recombinant cells can be derived from transgenic animals or can be made, used, and derived from in vitro cell culture. Further, cardiomyocytes can be normal but constructed to contain vectors that overexpress receptor RNA or protein or express variant receptor RNA or protein.

Mammalian cells include cellular test systems for ascertaining the effects of a given mutation on cell function, the function of a given mutation, the testing of compounds for the effect on a cell containing a given mutation, creating recombinant cells ex vivo for introduction into a subject, such as a transgenic animal or affected patient. In one embodiment, cells are derived from subjects or tissues known to be involved in cardiovascular disease or in the development of cardiovascular disease. Cells include, but are not limited to, cardiac myocytes and especially hypertrophic cardiac myocytes, other cells of the heart, cells from skeletal muscle, thymus, uterus, and prostate. In addition, cells appropriate for test systems can include fetal brain and placenta, as well as established cell lines, such as COS, HEK-293, and CHO cells.

The recombinant host cells are prepared by introducing the vector constructs described herein into the cells by techniques readily available to the person of ordinary skill in the art. These include, but are not limited to, calcium phosphate transfection, DEAE-dextran-mediated transfection, cationic lipid-mediated transfection, electroporation, transduction, infection, lipofection, and other techniques such as those found in Sambrook, et al. (*Molecular Cloning: A Laboratory Manual. 2nd, ed., Cold Spring Harbor Laboratory*, Cold Spring Harbor Laboratory Press, Cold Spring Harbor, N.Y., 1989).

Host cells can contain more than one vector. Thus, different nucleotide sequences can be introduced on different vectors of the same cell. Similarly, the receptor polynucleotides can be introduced either alone or with other polynucleotides that are not related to the receptor polynucleotides such as those providing trans-acting factors for expression vectors. When more than one vector is introduced into a cell, the vectors can be introduced independently, co-introduced or joined to the receptor polynucleotide vector.

In the case of bacteriophage and viral vectors, these can be introduced into cells as packaged or encapsulated virus by standard procedures for infection and transduction. Viral vectors can be replication-competent or replication-defective. In the case in which viral replication is defective, replication will occur in host cells providing functions that complement the defects.

Vectors generally include selectable markers that enable the selection of the subpopulation of cells that contain the recombinant vector constructs. The marker can be contained in the same vector that contains the polynucleotides described herein or may be on a separate vector. Markers include tetracycline or ampicillin-resistance genes for prokaryotic host cells and dihydrofolate reductase or neomycin resistance for eukaryotic host cells. However, any marker that provides selection for a phenotypic trait will be effective.

While the mature proteins can be produced in bacteria, yeast, mammalian cells, and other cells under the control of the appropriate regulatory sequences, cell-free transcription and translation systems can also be used to produce these proteins using RNA derived from the DNA constructs described herein.

Where secretion of the polypeptide is desired, appropriate secretion signals are incorporated into the vector. The signal sequence can be endogenous to the receptor polypeptides or heterologous to these polypeptides.

Where the polypeptide is not secreted into the medium, the protein can be isolated from the host cell by standard disruption procedures, including freeze thaw, sonication, mechanical disruption, use of lysing agents and the like. The polypeptide can then be recovered and purified by well-known purification methods including ammonium sulfate precipitation, acid extraction, anion or cationic exchange chromatography, phosphocellulose chromatography, hydrophobic-interaction chromatography, affinity chromatography, hydroxylapatite chromatography, lectin chromatography, or high performance liquid chromatography.

It is also understood that depending upon the host cell in recombinant production of the polypeptides described herein, the polypeptides can have various glycosylation patterns, depending upon the cell, or maybe non-glycosylated as when produced in bacteria. In addition, the polypeptides may include an initial modified methionine in some cases as a result of a host-mediated process.

Uses of Vectors and Host Cells

Specific Uses in Cardiovascular Disease

Host cells expressing the nucleic acids and polypeptides described herein, particularly recombinant host cells, have a variety of uses in the context of cardiovascular disease. Vectors and host cells provide cellular test systems for ascertaining the effect of a given mutation on the cellular phenotype. A desired mutant is introduced into a given host cell and assays are performed for cellular changes including biochemical, morphological, functional, gene expression, and the like. In another embodiment, a desired mutant is introduced into a given host cell and the function of a mutation can be assayed. In another embodiment, a desired mutant is introduced into a desired host cell and a compound is tested for its effect on gene expression, cellular changes, and the like. In a further embodiment, a desired mutant is introduced into a cell ex vivo so that the cell can be introduced back into its host, such as a transgenic animal or affected individual. In a further embodiment, a desired mutant is introduced into a host cell to prepare a transgenic host. Accordingly, preferred cells are derived from subjects with congestive heart failure or the risk of developing the disorder, or from tissues known to be involved in cardiovascular disease. Cells include, but are not limited to, cardiac myocytes, and especially hypertrophic cardiac myocytes, as well as other cells of the heart and associated vessels. It is further understood that the general uses of vectors and host cells described below also apply within the context of cardiovascular disease to cell types relevant to this type of disorder.

General Uses of Vectors and Host Cells

The host cells expressing the polypeptides described herein, and particularly recombinant host cells, have a variety of uses. First, the cells are useful for producing receptor proteins or polypeptides that can be further purified to produce desired amounts of receptor protein or fragments. Thus, host cells containing expression vectors are useful for polypeptide production.

Host cells are also useful for conducting cell-based assays involving the receptor or receptor fragments. Thus, a recombinant host cell expressing a native receptor is useful to assay for compounds that stimulate or inhibit receptor function. This includes ligand binding, gene expression at the level of transcription or translation, G-protein interaction, and components of the signal transduction pathway.

Host cells are also useful for identifying receptor mutants in which these functions are affected. If the mutants naturally occur and give rise to a pathology, host cells containing the mutations are useful to assay compounds that have a desired effect on the mutant receptor (for example, stimulating or inhibiting function) which may not be indicated by their effect on the native receptor.

Recombinant host cells are also useful for expressing the chimeric polypeptides described herein to assess compounds that activate or suppress activation by means of a heterologous amino terminal extracellular domain (or other binding region). Alternatively, a heterologous region spanning the entire transmembrane domain (or parts thereof) can be used to assess the effect of a desired amino terminal extracellular domain (or other binding region) on any given host cell. In this embodiment, a region spanning the entire transmembrane domain (or parts thereof) compatible with the specific host cell is used to make the chimeric vector. Alternatively, a heterologous carboxy terminal intracellular, e.g., signal transduction, domain can be introduced into the host cell.

Further, mutant receptors can be designed in which one or more of the various functions is engineered to be increased or decreased (e.g., ligand binding or G-protein binding) and used to augment or replace receptor proteins in an individual. Thus, host cells can provide a therapeutic benefit by replacing an aberrant receptor or providing an aberrant receptor that provides a therapeutic result. In one embodiment, the cells provide receptors that are abnormally active.

In another embodiment, the cells provide receptors that are abnormally inactive. These receptors can compete with endogenous receptors in the individual.

In another embodiment, cells expressing receptors that cannot be activated, are introduced into an individual in order to compete with endogenous receptors for ligand. For example, in the case in which excessive ligand is part of a treatment modality, it may be necessary to inactivate this ligand at a specific point in treatment. Providing cells that compete for the ligand, but which cannot be affected by receptor activation would be beneficial.

Homologously recombinant host cells can also be produced that allow the in situ alteration of endogenous receptor polynucleotide sequences in a host cell genome. This technology is more fully described in WO 93/09222, WO 91/12650 and U.S. Pat. No. 5,641,670. Briefly, specific polynucleotide sequences corresponding to the receptor polynucleotides or sequences proximal or distal to a receptor gene are allowed to integrate into a host cell genome by homologous recombination where expression of the gene can be affected. In one embodiment, regulatory sequences are introduced that either increase or decrease expression of an endogenous sequence. Accordingly, a receptor protein can be produced in a cell not normally producing it, or increased expression of receptor protein can result in a cell normally producing the protein at a specific level. Alternatively, the entire gene can be deleted. Still further, specific mutations can be introduced into any desired region of the gene to produce mutant receptor proteins. Such mutations could be introduced, for example, into the specific functional regions such as the ligand-binding site or the G-protein binding site.

In one embodiment, the host cell can be a fertilized oocyte or embryonic stem cell that can be used to produce a transgenic animal containing the altered receptor gene. Alternatively, the host cell can be a stem cell or other early tissue precursor that gives rise to a specific subset of cells and can be used to produce transgenic tissues in an animal. See also Thomas et al., *Cell* 51:503 (1987) for a description of homologous recombination vectors. The vector is introduced into an embryonic stem cell line (e.g., by electroporation) and cells in which the introduced gene has homologously recombined with the endogenous receptor gene is selected (see e.g., Li, E. et al., *Cell* 69:915 (1992). The selected cells are then injected into a blastocyst of an animal (e.g., a mouse) to form aggregation chimeras (see e.g., Bradley, A. in *Teratocarcinomas and Embryonic Stem Cells: A Practical Approach*, E. J. Robertson, ed. (IRL, Oxford, 1987) pp. 113-152). A chimeric embryo can then be implanted into a suitable pseudopregnant female foster animal and the embryo brought to term. Progeny harboring the homologously recombined DNA in their germ cells can be used to breed animals in which all cells of the animal contain the homologously recombined DNA by germline transmission of the transgene. Methods for constructing homologous recombination vectors and homologous recombinant animals are described further in Bradley, A. (1991) *Current Opinion in Biotechnology* 2:823-829 and in PCT International Publication Nos. WO 90/11354; WO 91/01140; and WO 93/04169.

The genetically engineered host cells can be used to produce non-human transgenic animals. A transgenic animal is preferably a mammal, for example a rodent, such as a rat or mouse, in which one or more of the cells of the animal include a transgene. A transgene is exogenous DNA which is integrated into the genome of a cell from which a transgenic animal develops and which remains in the genome of the mature animal in one or more cell types or tissues of the transgenic animal. These animals are useful for studying the function of a receptor protein and identifying and evaluating modulators of receptor protein activity.

Other examples of transgenic animals include non-human primates, sheep, dogs, cows, goats, chickens, and amphibians.

In one embodiment, a host cell is a fertilized oocyte or an embryonic stem cell into which receptor polynucleotide sequences have been introduced.

A transgenic animal can be produced by introducing nucleic acid into the male pronuclei of a fertilized oocyte, e.g., by microinjection, retroviral infection, and allowing the oocyte to develop in a pseudopregnant female foster animal. Any of the receptor nucleotide sequences can be introduced as a transgene into the genome of a non-human animal, such as a mouse.

Any of the regulatory or other sequences useful in expression vectors can form part of the transgenic sequence. This includes intronic sequences and polyadenylation signals, if not already included. A tissue-specific regulatory sequence(s) can be operably linked to the transgene to direct expression of the receptor protein to particular cells.

Methods for generating transgenic animals via embryo manipulation and microinjection, particularly animals such as mice, have become conventional in the art and are described, for example, in U.S. Pat. Nos. 4,736,866 and 4,870,009, both by Leder et al., U.S. Pat. No. 4,873,191 by Wagner et al. and in Hogan, B., *Manipulating the Mouse Embryo*, (Cold Spring Harbor Laboratory Press, Cold Spring Harbor, N.Y., 1986). Similar methods are used for production of other transgenic animals. A transgenic founder animal can be identified based upon the presence of the transgene in its genome and/or expression of transgenic mRNA in tissues or cells of the animals. A transgenic founder animal can then be used to breed additional animals carrying the transgene. Moreover, transgenic animals carrying a transgene can further be bred to other transgenic animals carrying other transgenes. A transgenic animal also includes animals in which the entire animal or tissues in the animal have been produced using the homologously recombinant host cells described herein.

In another embodiment, transgenic non-human animals can be produced which contain selected systems which allow for regulated expression of the transgene. One example of such a system is the cre/loxP recombinase system of bacteriophage P1. For a description of the cre/loxP recombinase system, see, e.g., Lakso et al. *PNAS* 89:6232-6236 (1992). Another example of a recombinase system is the FLP recombinase system of *S. cerevisiae* (O'Gorman et al. *Science* 251: 1351-1355 (1991). If a cre/loxP recombinase system is used to regulate expression of the transgene, animals containing transgenes encoding both the Cre recombinase and a selected protein is required. Such animals can be provided through the construction of "double" transgenic animals, e.g., by mating two transgenic animals, one containing a transgene encoding a selected protein and the other containing a transgene encoding a recombinase.

Clones of the non-human transgenic animals described herein can also be produced according to the methods described in Wilmut, I. et al. *Nature* 385:810-813 (1997) and PCT International Publication Nos. WO 97/07668 and WO 97/07669. In brief, a cell, e.g., a somatic cell, from the transgenic animal can be isolated and induced to exit the growth cycle and enter $G_o$ phase. The quiescent cell can then be fused, e.g., through the use of electrical pulses, to an enucleated oocyte from an animal of the same species from which the quiescent cell is isolated. The reconstructed oocyte is then cultured such that it develops to morula or blastocyst and then transferred to a pseudopregnant female foster animal. The offspring born of this female foster animal will be a clone of the animal from which the cell, e.g., the somatic cell, is isolated.

Transgenic animals containing recombinant cells that express the polypeptides described herein are useful to conduct the assays described herein in an in vivo context. Accordingly, the various physiological factors that are present in vivo and that could effect ligand binding, receptor activation, and signal transduction, may not be evident from in vitro cell-free or cell-based assays. Accordingly, it is useful to provide non-human transgenic animals to assay in vivo receptor function, including ligand interaction, the effect of specific mutant receptors on receptor function and ligand interaction, and the effect of chimeric receptors. It is also possible to assess the effect of null mutations, that is mutations that substantially or completely eliminate one or more receptor functions.

Pharmaceutical Compositions

The receptor nucleic acid molecules, protein (particularly fragments such as the amino terminal extracellular domain), modulators of the protein, and antibodies (also referred to herein as "active compounds") can be incorporated into pharmaceutical compositions suitable for administration to a subject, e.g., a human. Such compositions typically comprise the nucleic acid molecule, protein, modulator, or antibody and a pharmaceutically acceptable carrier.

As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, such media can be used in the compositions of the invention. Supplementary active compounds can also be incorporated into the compositions. A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound (e.g., a receptor protein or anti-receptor antibody) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For oral administration, the agent can be contained in enteric forms to survive the stomach or further coated or mixed to be released in a particular region of the GI tract by known methods. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. "Dosage unit form" as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

The nucleic acid molecules of the invention can be inserted into vectors and used as gene therapy vectors. Gene therapy vectors can be delivered to a subject by, for example, intravenous injection, local administration (U.S. Pat. No. 5,328,470) or by stereotactic injection (see e.g., Chen et al., *PNAS* 91:3054-3057 (1994)). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g. retroviral vectors, the pharmaceutical preparation can include one or more cells which produce the gene delivery system.

The pharmaceutical compositions can be included in a container, pack, or dispenser together with instructions for administration.

This invention may be embodied in many different forms and should not be construed as limited to the embodiments set forth herein; rather, these embodiments are provided so that this disclosure will fully convey the invention to those skilled in the art. Many modifications and other embodiments of the invention will come to mind in one skilled in the art to which this invention pertains having the benefit of the teachings presented in the foregoing description. Although specific terms are employed, they are used as in the art unless otherwise indicated.

EXAMPLE I

To further explore the function of the novel G-protein coupled receptor in cardiac hypertrophy, several independent sets of transgenic mice were made in which the receptor could be specifically overexpressed in cardiomyocytes. Expression constructs included the alpha-MHC promoter operably linked to the receptor coding sequence. This cardiomyocyte specific promoter is well-characterized in the art. Constructs were also designed in which a CMV promoter was operably linked to the receptor coding sequence. The results of these experiments show that transgenic mice specifically overexpressing the novel receptor gene develop cardiomyocyte hypertrophy. Many of these died from heart failure.

An antibody directed against a C-terminal peptide (SEQ ID NO:12, corresponds to amino acids 348-361 of SEQ ID NO:1 ), DTSVKRNDLSIISG, was used to detect receptor expression in wild type and transgenic (F1) mice. Protein was extracted from hearts of control and transgenic animals. The result showed that the C-terminal antibody could identify the protein in a heart protein extract from transgenic mice in which the receptor gene is expressed from the alpha-MHC promoter. In contrast, no signal was detected in non-transgenic control animals.

A heart-body weight ratio was assessed in animals affected by overexpression of the receptor gene product. The ratio was significantly higher in a significant number of affected mice. The ratios ranged from approximately 1.5 to approximately 2.7. It was also noted that in the affected mice, overexpression of the gene detrimentally affected alertness. Further, pathology results showed an enlargement of the atrium as well as ventricle thrombosis in the atrium. In addition, edema in the chest and breathing difficulties were observed.

Histopathology of the hearts from affected animals showed biventricular dilatation, cardiomyocyte hypertrophy, atrial thrombi, and interstitial fibrosis.

EXAMPLE II

The 14273 receptor was shown to be upregulated in a rat pressure overload model, as seen by in situ hybridization. The model was generated by placing a constrictive band around the aorta to induce a state of cardiac hypertrophy. The receptor was shown to be induced at the RNA level by 22 weeks following banding of the aorta. This increase in expression was correlated with the hypertrophic phenotype. Independent results were obtained with two independent mouse probes. Accordingly, the expression of the receptor is induced in the failed heart, collected 22 weeks after aortic banding, using a non-banded control heart as a comparison.

Sections (10 μm for embryos and 8 μm for organ sections) were postfixed with 4% formaldehyde in DEPC-treated 1× phosphate-buffered saline at room temperature for 10 minutes before being rinsed twice in DEPC-treated 1× phosphate-buffered saline and once in 0.1 M triethanolamine-HCl (pH 8.0). Following incubation in 0.25% acetic anhydride-0.1 M triethanolamine-HCl for 10 minutes, sections were rinsed in DEPC-treated 2×SSC (1×SSC is 0.15M NaCl plus 0.015M sodium citrate). Tissue was dehydrated through a series of ethanol washes, incubated in 100% chloroform for 5 minutes, and then rinsed in 100% ethanol for 1 minute and 95% ethanol for 1 minute and allowed to air dry.

The hybridization was performed using a $^{35}$S-radiolabeled cRNA probe.

The sequence of two mouse probes used for in situ hybridization of 14273:

```
TGTGGAGTCCCATCATCATCACCATCCTCCTCATCTTGATCCAAAACTTC
CGGCAGGACCTGGTCATCTGGCCATCCCTTTTCTTCTGGGTGGTGGCCTT
```

-continued
```
CACGTTTGCCAACTCTGCCCTAAACCCCATACTGTACAACATGTCGCTGT
TCAGGAACGAATGGAGGAAGATTTTTTGCTG (SEQ ID NO:14,
corresponds to nucleotides 1021-1201 of SEQ ID NO:
5)

AAGAGGCTTACGCTGAGCTTGGCATACTCTGAGAGCCACCAGATCCGAGT
GTCCCAACAAGACTACCGACTCTTCCGCACGCTCTTCCTGCTCATGGTTT
CCTTCTTCATCATGTGGAGTCCCATCATCATCACCATC (SEQ ID NO:
15, corresponds to nucleotides 909-1036 of SEQ ID
NO:5)
```

EXAMPLE III

Transgenic mice expressing the 14273 receptor were shown to develop heart failure. Receptor mRNA and protein levels were correlated with the severity of the phenotype. The sequence of events were: hypertrophy (both nuclear and cytoplasmic) of cardiomyocytes, development of eosinophilic nuclei (a hallmark of hypertrophy), myocyte disorganization, atrial and ventricular loss of myocytes, interstitial fibrosis, fibroelastosis, and thrombosis. Four transgenic lines showed severe symptoms, with pathology or death in every member studied, generally in weeks. In this group, relatively high RNA and protein expression was observed.

In a second group, pathology or death was observed, but not in all of the animals, in a space of weeks to around three months. In this group, expression levels of the receptor were lower than those with the first group, which had the most severe symptoms.

In the third group, the transgenic mice showed no detectable symptoms. However, the histological results showed cardiohypertrophy with various degrees at the age of two to four months. The expression levels of the receptor in this group were the lowest among the three groups of transgenic mice.

In Northern blots developed against tissues from each of these groups, high expression of the receptor was observed compared to a wild-type control. In each of these samples, the expression of atrial natriuretic factor, ANF, was also shown to be increased, relative to expression in wild-type controls.

That which is claimed:

1. A method for identifying a compound which binds to a polypeptide selected from the group consisting of:
   (a) an isolated polypeptide comprising the amino acid sequence shown in SEQ ID NO:1;
   (b) an isolated polypeptide comprising the amino acid sequence encoded by the nucleotide sequence of SEQ ID NO:2; and
   (c) an isolated polypeptide comprising an amino acid sequence that is at least 95% identical to the amino acid sequence shown in SEQ ID NO:1, the method comprising:
   i) contacting the polypeptide, or a cell expressing the polypeptide with a test compound under conditions that allow the compound to bind the polypeptide,
   ii) detecting the binding of the test compound to the polypeptide, thereby identifying a compound which binds the polypeptide.

2. The method of claim 1, wherein the binding of the test compound to the polypeptide is detected by a method selected from the group consisting of:
   a) direct detection of test compound/polypeptide binding;
   b) a competition binding assay; and
   c) an immunoassay.

3. The method of claim 1, wherein the test compound is selected from the group consisting of a peptide, phosphopeptide, antibody, and a small molecule.

4. The method of claim 1, wherein the test compound is labeled.

* * * * *

SEQUENCE LISTING

<160> NUMBER OF SEQ ID NOS: 15

<210> SEQ ID NO 1
<211> LENGTH: 361
<212> TYPE: PRT
<213> ORGANISM: Homo sapiens

<400> SEQUENCE: 1

Met Ser Pro Glu Cys Ala Arg Ala Ala Gly Asp Ala Pro Leu Arg Ser
1               5                   10                  15

Leu Glu Gln Ala Asn Arg Thr Arg Phe Pro Phe Ser Asp Val Lys
            20                  25                  30

Gly Asp His Arg Leu Val Leu Ala Ala Val Glu Thr Thr Val Leu Val
        35                  40                  45

Leu Ile Phe Ala Val Ser Leu Leu Gly Asn Val Cys Ala Leu Val Leu
    50                  55                  60

Val Ala Arg Arg Arg Arg Arg Gly Ala Thr Ala Cys Leu Val Leu Asn
65                  70                  75                  80

Leu Phe Cys Ala Asp Leu Leu Phe Ile Ser Ala Ile Pro Leu Val Leu
              85                  90                  95

Ala Val Arg Trp Thr Glu Ala Trp Leu Leu Gly Pro Val Ala Cys His
            100                 105                 110

Leu Leu Phe Tyr Val Met Thr Leu Ser Gly Ser Val Thr Ile Leu Thr
            115                 120                 125

Leu Ala Ala Val Ser Leu Glu Arg Met Val Cys Ile Val His Leu Gln
            130                 135                 140

Arg Gly Val Arg Gly Pro Gly Arg Arg Ala Arg Ala Val Leu Leu Ala
45                  150                 155                 160

Leu Ile Trp Gly Tyr Ser Ala Val Ala Ala Leu Pro Leu Cys Val Phe
                165                 170                 175

Phe Arg Val Val Pro Gln Arg Leu Pro Gly Ala Asp Gln Glu Ile Ser
            180                 185                 190

Ile Cys Thr Leu Ile Trp Pro Thr Ile Pro Gly Glu Ile Ser Trp Asp
            195                 200                 205

Val Ser Phe Val Thr Leu Asn Phe Leu Val Pro Gly Leu Val Ile Val
            210                 215                 220

Ile Ser Tyr Ser Lys Ile Leu Gln Ile Thr Lys Ala Ser Arg Lys Arg
25                  230                 235                 240

Leu Thr Val Ser Leu Ala Tyr Ser Glu Ser His Gln Ile Arg Val Ser
                245                 250                 255

Gln Gln Asp Phe Arg Leu Phe Arg Thr Leu Phe Leu Leu Met Val Ser
            260                 265                 270

Phe Phe Ile Met Trp Ser Pro Ile Ile Thr Ile Leu Leu Ile Leu
            275                 280                 285

Ile Gln Asn Phe Lys Gln Asp Leu Val Ile Trp Pro Ser Leu Phe Phe
            290                 295                 300

Trp Val Val Ala Phe Thr Phe Ala Asn Ser Ala Leu Asn Pro Ile Leu
05                  310                 315                 320

Tyr Asn Met Thr Leu Cys Arg Asn Glu Trp Lys Lys Ile Phe Cys Cys
                325                 330                 335

Phe Trp Phe Pro Glu Lys Gly Ala Ile Leu Thr Asp Thr Ser Val Lys
            340                 345                 350

Arg Asn Asp Leu Ser Ile Ile Ser Gly
            355                 360

<210> SEQ ID NO 2
<211> LENGTH: 1743
<212> TYPE: DNA
<213> ORGANISM: Homo sapiens

<400> SEQUENCE: 2
tccggactag ttctagaccg ctgcgggccg ccaggcgccg ggaatgtccc ctgaatgcgc      60
gcgggcagcg ggcgacgcgc ccttgcgcag cctggagcaa gccaaccgca cccgctttcc     120
cttcttctcc gacgtcaagg gcgaccaccg gctggtgctg gccgcggtgg agacaaccgt     180
gctggtgctc atctttgcag tgtcgctgct gggcaacgtg tgcgccctgg tgctggtggc     240
gcgccgacga cgccgcggcg cgactgcctg cctggtactc aacctcttct gcgcggacct     300
gctcttcatc agcgctatcc ctctggtgct ggccgtgcgc tggactgagg cctggctgct     360
gggcccccgt tgcctgccac ctgctcttct acgtgatgac ctgagcggca gcgtcaccat     420
cctcacgctg gccgcggtca gcctggagcg catggtgtgc atcgtgcacc tgcagcgcgg     480

-continued

```
cgtgcgggt cctgggcggc gggcgcgggc agtgctgctg gcgctcatct ggggctattc    540
ggcggtcgcc gctctgcctc tctgcgtctt ctttcgagtc gtcccgcaac ggctccccgg    600
cgccgaccag gaaatttcga tttgcacact gatttggccc accattcctg agagatctc    660 gtgggatgtc tcttttgtta ctttgaactt cttggtgcca ggactggtca ttgtgatcag    720
ttactccaaa attttacaga tcacaaaggc atcaaggaag aggctcacgg taagcctggc    780
ctactcggag agccaccaga tccgcgtgtc ccagcaggac ttccggctct ccgcacct     840 cttcctcctc atggtctcct tcttcatcat gtggagcccc atcatcatca ccatcctcct    900
catcctgatc agaacttca agcaagacct ggtcatctgg ccgtccctct tcttctgggt    960
ggtggccttc acatttgcta attcagccct aaaccccatc tctacaaca tgacactgtg   1020 caggaatgag tggaagaaaa ttttttgctg cttctggttc ccagaaaagg gagccatttt   1080
aacagacaca tctgtcaaaa gaaatgactt gtcgattatt tctggctaat ttttctttat   1140
agccgagttt ctcacacctg cgagctgtg gcatgctttt aaacagagtt catttccagt   1200
accctccatc agtgcaccct gctttaagaa atgaaccta tgcaaataga catccacagc   1260
gtcggtaaat taagggggtga tcaccaagtt tcataatatt ttcccttttat aaaaggatt    1320 gttggccagg tgcagtggtt catgcctgta atcccagcag tttgggaggc tgaggtgggt   1380
ggatcacctg aggtcaggag ttcgagacca acctgaccaa catggtgaga cccccgtctc   1440
tactaaaaat aaaaaaaaaa attagctggg agtggtggtg ggcacctgta atcctagcta   1500
cttgggaggc tgaaccagga gaatctcttg aacctgggag gcagaggttg cagtgagccg   1560
agatcgtgcc attgcactcc aaccagggca acaagagtga aactccatct aaaaaaaaa    1620 aaaaaaaga tttgttatgg gttccttta aatgtgaact tttttagtgt gtttgtaata     1680
tgatcaaatt taataaatat ttatttatga ctgttcagca aaaaaaaaa aaaaaaggg      1740 cgg                                                                1743
```

<210> SEQ ID NO 3
<211> LENGTH: 259
<212> TYPE: PRT
<213> ORGANISM: Unknown
<220> FEATURE:
<223> OTHER INFORMATION: Description of Unknown Organism: Seven
      Transmembrane Segment Rhodopsin Superfamily

<400> SEQUENCE: 3

```
Gly Asn Leu Leu Val Ile Leu Val Ile Leu Arg Thr Lys Lys Leu Arg
 1               5                  10                  15

Thr Pro Thr Asn Ile Phe Ile Leu Asn Leu Ala Val Ala Asp Leu Leu
            20                  25                  30

Phe Leu Leu Thr Leu Pro Pro Trp Ala Leu Tyr Tyr Leu Val Gly Gly
        35                  40                  45

Ser Glu Asp Trp Pro Phe Gly Ser Ala Leu Cys Lys Leu Val Thr Ala
    50                  55                  60

Leu Asp Val Val Asn Met Tyr Ala Ser Ile Leu Leu Thr Ala Ile
65                  70                  75                  80

Ser Ile Asp Arg Tyr Leu Ala Ile Val His Pro Leu Arg Tyr Arg Arg
                85                  90                  95

Arg Arg Thr Ser Pro Arg Arg Ala Lys Val Val Ile Leu Leu Val Trp
            100                 105                 110

Val Leu Ala Leu Leu Leu Ser Leu Pro Pro Leu Leu Phe Ser Trp Val
        115                 120                 125
```

```
Lys Thr Val Glu Glu Gly Asn Gly Thr Leu Asn Val Asn Val Thr Val
            130                 135                 140

Cys Leu Ile Asp Phe Pro Glu Glu Ser Thr Ala Ser Val Ser Thr Trp
145                 150                 155                 160

Leu Arg Ser Tyr Val Leu Leu Ser Thr Leu Val Gly Phe Leu Leu Pro
                165                 170                 175

Leu Leu Val Ile Leu Val Cys Tyr Thr Arg Ile Leu Arg Thr Leu Arg
            180                 185                 190

Lys Ala Ala Lys Thr Leu Leu Val Val Val Val Phe Val Leu Cys
            195                 200                 205

Trp Leu Pro Tyr Phe Ile Val Leu Leu Leu Asp Thr Leu Cys Leu Ser
210                 215                 220

Ile Ile Met Ser Ser Thr Cys Glu Leu Glu Arg Val Leu Pro Thr Ala
225                 230                 235                 240

Leu Leu Val Thr Leu Trp Leu Ala Tyr Val Asn Ser Cys Leu Asn Pro
                245                 250                 255

Ile Ile Tyr

<210> SEQ ID NO 4
<211> LENGTH: 361
<212> TYPE: PRT
<213> ORGANISM: Murine ortholog

<400> SEQUENCE: 4

Met Ser Pro Glu Cys Ala Gln Thr Thr Gly Pro Gly Pro Ser His Thr
1               5                   10                  15

Leu Asp Gln Val Asn Arg Thr His Phe Pro Phe Phe Ser Asp Val Lys
                20                  25                  30

Gly Asp His Arg Leu Val Leu Ser Val Val Glu Thr Val Leu Gly
            35                  40                  45

Leu Ile Phe Val Val Ser Leu Leu Gly Asn Val Cys Ala Leu Val Leu
        50                  55                  60

Val Ala Arg Arg Arg Arg Gly Ala Ser Ala Ser Leu Val Leu Asn
65                  70                  75                  80

Leu Phe Cys Ala Asp Leu Leu Phe Thr Ser Ala Ile Pro Leu Val Leu
                85                  90                  95

Val Val Arg Trp Thr Glu Ala Trp Leu Leu Gly Pro Val Val Cys His
                100                 105                 110

Leu Leu Phe Tyr Val Met Thr Met Ser Gly Ser Val Thr Ile Leu Thr
            115                 120                 125

Leu Ala Ala Val Ser Leu Glu Arg Met Val Cys Ile Val Arg Leu Arg
        130                 135                 140

Arg Gly Leu Ser Gly Pro Gly Arg Arg Thr Gln Ala Ala Leu Leu Ala
145                 150                 155                 160

Phe Ile Trp Gly Tyr Ser Ala Leu Ala Ala Leu Pro Leu Tyr Ile Leu
                165                 170                 175

Phe Arg Val Val Pro Gln Arg Leu Pro Gly Gly Asp Gln Glu Ile Pro
            180                 185                 190

Ile Cys Thr Leu Asp Trp Pro Asn Arg Ile Gly Glu Ile Ser Trp Asp
        195                 200                 205

Val Phe Phe Glu Thr Leu Asn Phe Leu Val Pro Gly Leu Val Ile Val
    210                 215                 220

Ile Ser Tyr Ser Lys Ile Leu Gln Ile Thr Lys Ala Ser Arg Lys Arg
225                 230                 235                 240
```

```
Leu Thr Leu Ser Leu Ala Tyr Ser Glu Ser His Gln Ile Arg Val Ser
                245                 250                 255

Gln Gln Asp Tyr Arg Leu Phe Arg Thr Leu Phe Leu Leu Met Val Ser
            260                 265                 270

Phe Phe Ile Met Trp Ser Pro Ile Ile Thr Ile Leu Leu Ile Leu
        275                 280                 285

Ile Gln Asn Phe Arg Gln Asp Leu Val Ile Trp Pro Ser Leu Phe Phe
    290                 295                 300

Trp Val Val Ala Phe Thr Phe Ala Asn Ser Ala Leu Asn Pro Ile Leu
305                 310                 315                 320

Tyr Asn Met Ser Leu Phe Arg Asn Glu Trp Arg Lys Ile Phe Cys Cys
                325                 330                 335

Phe Phe Phe Pro Glu Lys Gly Ala Ile Phe Thr Asp Thr Ser Val Arg
            340                 345                 350

Arg Asn Asp Leu Ser Val Ile Ser Ser
            355                 360

<210> SEQ ID NO 5
<211> LENGTH: 1560
<212> TYPE: DNA
<213> ORGANISM: Murine ortholog

<400> SEQUENCE: 5
ttgccaagct cagcgtaagc ctcttccact gcaatctcac agaagggggtt catggagtgc        60 ttcacaccat cagtgaccac tccagacttg tccggcttta cccgaatctt cacagcggag       120
tcgatgaccc tcttgacagc cacgagcgcg cgcagctccg ccatcttccc ggacgcgtgg       180
gccgggcgcc cggcatgtcc cctgagtgtg cacagacgac gggccctggt ccctcgcaca       240
ccctggacca agtcaatcgc acccacttcc ctttcttctc ggatgtcaag ggcgaccacc       300
ggttggtgtt gagcgtcgtg gagaccaccg ttctgggact catctttgtc gtctcactgc       360
tgggcaacgt gtgtgctcta gtgctggtgg cgcgccgtcg gcgccgtggg gcgtcagcca       420
gcctggtgct caacctcttc tgcgcggatt gctcttcac cagcgccatc cctctagtgc        480
tcgtcgtgcg ctggactgag gcctggctgt tggggcccgt cgtctgccac ctgctcttct       540
acgtgatgac aatgagcggc agcgtcacga tcctcacact ggccgcggtc agcctggagc       600
gcatggtgtg catcgtgcgc ctccggcgcg gcttgagcgg ccgggggcgg cggactcagg       660
cggcactgct ggctttcata tggggttact cggcgctcgc cgcgctgccc ctctacatct       720
tgttccgcgt ggtcccgcag cgccttcccg gcggggacca ggaaattccg atttgcacat       780 ggattggcc caaccgcata ggagaaatct catgggatgt gttttttgag actttgaact       840
tcctggtgcc gggactggtc attgtgatca gttactccaa aattttacag atcacgaaag       900
catcgcggaa gaggcttacg ctgagcttgg catactctga gagccaccag atccgagtgt       960
cccaacaaga ctaccgactc ttccgcacgc tcttcctgct catggtttcc ttcttcatca      1020
tgtggagtcc catcatcatc accatcctcc tcatcttgat ccaaaacttc cggcaggacc      1080
tggtcatctg gccatccctt ttcttctggg tggtggcctt cacgtttgcc aactctgccc      1140
taaaccccat actgtacaac atgtcgctgt tcaggaacga atggaggaag attttttgct      1200
gcttcttttt tccagagaag ggagccattt ttacagatac gtctgtcagg cgaaatgact      1260
tgtctgttat ttccagctaa ctagcctctg gtgccaggtg aaccacggtg tgcatgtaaa      1320
gggagttaac ttcaaggaaa gcccaccagt gcgccctgct ttaaaaatac ccgacttcca      1380
acagcaggca tctacggagc cagcaaatta aggaatgatc gctcagtata aaatatttt       1440
```

```
tccttaaaag aactttctat gggttccttt tgtgaacttt tttaagtgtg tttgtaatat    1500
gatctagtta ataaatttt atttataacg tgttcctaca aaaaaaaaaa aaaaaaaaaa    1560
```

<210> SEQ ID NO 6
<211> LENGTH: 6
<212> TYPE: PRT
<213> ORGANISM: Artificial Sequence
<220> FEATURE:
<223> OTHER INFORMATION: Motif: N-myristoylation site

<400> SEQUENCE: 6

Gly Asn Val Cys Ala Leu
 1               5

<210> SEQ ID NO 7
<211> LENGTH: 6
<212> TYPE: PRT
<213> ORGANISM: Artificial Sequence
<220> FEATURE:
<223> OTHER INFORMATION: Motif: N-myristoylation site

<400> SEQUENCE: 7

Gly Ala Thr Ala Cys Leu
 1               5

<210> SEQ ID NO 8
<211> LENGTH: 6
<212> TYPE: PRT
<213> ORGANISM: Artificial Sequence
<220> FEATURE:
<223> OTHER INFORMATION: Motif: N-myristoylation site

<400> SEQUENCE: 8

Gly Ala Ile Leu Thr Asp
 1               5

<210> SEQ ID NO 9
<211> LENGTH: 22
<212> TYPE: PRT
<213> ORGANISM: Artificial Sequence
<220> FEATURE:
<223> OTHER INFORMATION: Motif: N-myristoylation site

<400> SEQUENCE: 9

Leu Gly Pro Val Ala Cys His Leu Leu Phe Tyr Val Met Thr Leu Ser
 1               5                  10                  15

Gly Ser Val Thr Ile Leu
            20

<210> SEQ ID NO 10
<211> LENGTH: 6
<212> TYPE: PRT
<213> ORGANISM: Artificial Sequence
<220> FEATURE:
<223> OTHER INFORMATION: Motif: N-myristoylation site

<400> SEQUENCE: 10

```
Gly Ala Ser Ala Ser Leu
1               5

<210> SEQ ID NO 11
<211> LENGTH: 6
<212> TYPE: PRT
<213> ORGANISM: Artificial Sequence
<220> FEATURE:
<223> OTHER INFORMATION: Motif: N-myristoylation site

<400> SEQUENCE: 11

Gly Ala Ile Phe Thr Asp
1               5

<210> SEQ ID NO 12
<211> LENGTH: 14
<212> TYPE: PRT
<213> ORGANISM: Artificial Sequence
<220> FEATURE:
<223> OTHER INFORMATION: Antigenic Segment

<400> SEQUENCE: 12

Asp Thr Ser Val Lys Arg Asn Asp Leu Ser Ile Ile Ser Gly
1               5                   10

<210> SEQ ID NO 13
<211> LENGTH: 14
<212> TYPE: PRT
<213> ORGANISM: Homo sapiens

<400> SEQUENCE: 13

Asp Thr Ser Val Lys Arg Asn Asp Leu Ser Ile Ile Ser Gly
1               5                   10

<210> SEQ ID NO 14
<211> LENGTH: 181
<212> TYPE: DNA
<213> ORGANISM: Mus musculus

<400> SEQUENCE: 14
tgtggagtcc catcatcatc accatcctcc tcatcttgat ccaaaacttc cggcaggacc      60
tggtcatctg gccatccctt ttcttctggg tggtggcctt cacgtttgcc aactctgccc     120
taaaccccat actgtacaac atgtcgctgt tcaggaacga atggaggaag attttttgct     180
g                                                                    181

<210> SEQ ID NO 15
<211> LENGTH: 138
<212> TYPE: DNA
<213> ORGANISM: Mus musculus

<400> SEQUENCE: 15
aagaggctta cgctgagctt ggcatactct gagagccacc agatccgagt gtcccaacaa      60
gactaccgac tcttccgcac gctcttcctg ctcatggttt ccttcttcat catgtggagt     120
cccatcatca tcaccatc                                                  138
```